: US 8,007,806 B2
: Aug. 30, 2011

(12) United States Patent
Morein et al.

(54) VACCINE COMPOSITION COMPRISING A FIBRONECTIN BINDING PROTEIN OR A FIBRONECTIN BINDING PEPTIDE

(75) Inventors: Bror Morein, Uppsala (SE); Karin Lövgren-Bengtsson, Uppsala (SE); Katarina Ranlund, Uppsala (SE); Birgitta Fromgren, Uppsala (SE); Jill Ekstrom, Alunda (SE); Carlos Concha Baschunan, Santiago (CL)

(73) Assignee: Isconova AB, Uppsala (SE)

( * ) Notice: Subject to any disclaimer, the term of this patent is extended or adjusted under 35 U.S.C. 154(b) by 285 days.

(21) Appl. No.: 11/795,662

(22) PCT Filed: Jan. 20, 2006

(86) PCT No.: PCT/SE2006/000082
§ 371 (c)(1),
(2), (4) Date: Jun. 2, 2008

(87) PCT Pub. No.: WO2006/078213
PCT Pub. Date: Jul. 27, 2006

(65) Prior Publication Data
US 2009/0208562 A1 Aug. 20, 2009

Related U.S. Application Data

(60) Provisional application No. 60/593,504, filed on Jan. 20, 2005.

(51) Int. Cl.
*A61K 39/00* (2006.01)
*A61K 39/02* (2006.01)
*A61K 39/385* (2006.01)
*A61K 45/00* (2006.01)

(52) U.S. Cl. ............... 424/184.1; 424/193.1; 424/234.1; 424/278.1

(58) Field of Classification Search .................. None
See application file for complete search history.

(56) References Cited

U.S. PATENT DOCUMENTS

| 4,900,549 | A | 2/1990 | De Vries et al. |
| 5,057,540 | A | 10/1991 | Kensil et al. |
| 5,270,168 | A | 12/1993 | Grinnell |
| 5,540,933 | A | 7/1996 | Ruoslahti et al. |
| 5,618,916 | A | 4/1997 | Ratliff et al. |
| 5,620,690 | A | 4/1997 | Kersten et al. |
| 5,679,354 | A | 10/1997 | Morein et al. |
| 5,753,235 | A | 5/1998 | Haanes et al. |
| 5,925,359 | A | 7/1999 | Van Woensel et al. |
| 6,177,081 | B1 | 1/2001 | Wechter et al. |
| 6,231,859 | B1 | 5/2001 | Kensil |
| 6,288,214 | B1 * | 9/2001 | Hook et al. ............... 530/387.1 |
| 6,352,697 | B1 | 3/2002 | Cox et al. |
| 6,428,807 | B1 | 8/2002 | MacFarlan et al. |
| 6,558,670 | B1 | 5/2003 | Friede et al. |
| 7,838,019 | B2 | 11/2010 | Morein et al. |
| 2006/0121065 | A1 | 6/2006 | Morein et al. |
| 2006/0239963 | A1 | 10/2006 | Morein et al. |

FOREIGN PATENT DOCUMENTS

| EP | 0 109 942 A2 | 5/1984 |
| EP | 0440289 A1 | 8/1991 |
| EP | 0 362 279 B1 | 1/1995 |
| WO | 88/09336 A1 | 12/1988 |
| WO | 90/03184 A1 | 4/1990 |
| WO | WO-9103572 A1 | 3/1991 |
| WO | 96/11711 A1 | 4/1996 |
| WO | 97/30728 A1 | 8/1997 |
| WO | 98/36772 A1 | 8/1998 |
| WO | 2004/004762 | 1/2004 |
| WO | WO-2004004762 A1 | 1/2004 |
| WO | 2004/030696 A2 | 4/2004 |
| WO | 2005002620 | 1/2005 |
| WO | WO-2005002620 A1 | 1/2005 |

OTHER PUBLICATIONS

"European Application Serial No. 06701328.4, Communication mailed Jan. 22, 2010", 4 pgs.
Pearse, M. J., et al., "ISCOMATRIX® adjuvant for antigen delivery", *Advanced Drug Delivery Reviews*, 57, (2005), 465-474.
"European Application Serial No. 06701328.4, Communication and Supplementary European Search Report mailed Oct. 9, 2008", 7 pgs.
Brennan, Frank R., et al., "Chimeric Plant Virus Particles Administered Nasally or Orally Induce Systemic and Mucosal Immune Responses in Mice", *Journal of Virology*, vol. 73, No. 2, (Feb. 1999), 930-938.
McArthur, J., et al., "Immune responses of a liposome/ISCOM vaccine adjuvant against streptococcal fibronectin binding protein 1 (Sfb1) in mice", *Indian J Med Res 119*, (Suppl), (May 2004), 115-120.
Nelson, L., et al., "Adhesins in *Staphylococcal mastitis* as Vaccine Components", *Flemish Veterinary Journal*, vol. 62, Suppl. 1, Chapter 8, (1991), 111-125.

(Continued)

*Primary Examiner* — Albert Navarro
(74) *Attorney, Agent, or Firm* — Pearne & Gordon LLP

(57) ABSTRACT

The present invention relates to a composition comprising at least one fibronectin binding protein, and/or at least one a truncated fibronectin binding protein and/or at least one fibronectin binding peptide, all comprising at least one fibronectin binding domain; and at least one Iscom matrix complex and/or liposome and/or at least one lipid and at least one saponin, whereby the at least one lipid and the at least one saponin may be in complex, solution or suspension. Further, it regards use thereof for the production of a vaccine against a micro organism that comprises at least one one fibronectin binding domain. It also regards a kit of parts comprising at least two compartments, wherein one compartment comprises at least one truncated fibronectin binding protein and/or a fibronectin binding peptide, that comprises at least one fibronectin binding domain, and another compartment comprises an instruction for use and/or an Iscom matrix complex and/or an iscom complex and or a liposome. Further it relates to a method for vaccination of an individual.

22 Claims, 11 Drawing Sheets

OTHER PUBLICATIONS

"Chinese Application Serial No. 20060002650.3, Second Office Action dated Feb. 5, 2010", (English Translation), 16 pgs.
"Safety Evaluation of Certain Food Additives and Contaminants Quillaja Extracts, "WHO food Additives Series: 48, 2002.
Morein, B. et al.; Iscom, A Novel Structure for Antigenic Presentation of Membrane Proteins from Enveloped Viruses; Nature, vol. 308, No. 5958, Mar. 29, 1984; pp. 457-460; Macmillan Journals Ltd., 1984.
Pierre Tiollais, Christine Pourcel & Anne Dejean, "The Hepatitis B Virus", Oct. 10, 1985, Nature, vol. 317, pp. 489-495.
Chavali S., et al., Adjuvant Effects of Orally Administered Saponins on Humoral and Cellular Immune Responses in Mice; Immunobiol., vol. 174, Mar. 2, 1987, pp. 347-359.
Chavali S., et al., An Invitro Study of Immunomodulatory Effects of Some Saponins; International Society for Immunopharmacology, vol. 9, No. 6, Mar. 24, 1987, Great Britain, pp. 675-683.
Pyle, S.W., Morein, B., Bess, J.W., Akerblom, L., Nara, P.L., Nigida, S.M., Lerche, N.W., Robey, W.G., Fischinger, P. J., and Arthur, L.O., "Immune Response to Immunostimulatory Complexes (ISCOMS) Prepared from Human Immunodeficiency Virus Type 1 (HIV-1) or the HIV-1 External Envelope Glycoprotein (gp120)," Vaccine, vol. 7, 1989, 465-473.
Takahashi, Hidemi et al., Inductin of CD8 Cytotoxic T Cells by Immunization with Purified HIV-1 Envelope Protein in ISCOMs; Nature, vol. 344, Apr. 26, 1990; pp. 873-875.
Fohlman, Jan et al., Vaccination of Balb/c mice against enteroviral mediated myocarditis; Vaccine, vol. 8, Aug. 1990; Butterworth-Heineman Ltd; pp. 381-384.
P.G.W. Plagemann, "Hepatitis C Virus", Jun. 4, 1991, Arch Virol, vol. 120, pp. 165-180.
Gupta et al., "Adjuvants-a balance between toxicity and adjuvanticity," Vaccine, vol. 11 No. 3, pp. 293-306 (1993).
Lipford et al., "Vaccination with immunodominant peptides encapsulated in Quil A-containing liposomes induces peptide-specific primary CD8+ cytoxtoxic T cells," Vaccine, vol. 12 No. 1, pp. 73-80 (Jan. 1994).
Sjolander, A. Bengtsson, K.L., Johansson, M. and Morein, B., "Kinetics, Localization and Isotype Profile of Antibody Responses to Immune Stimulating Complexes (ISCOMS) Containing Human Influenza Virus Envelope Glycoproteins," Scand. J. Immunol. 43, 1996, 164-172.
Barr, Ian G., et al., ISCOMs (immunostimulating complexes): The first decade; CSL Limited, Parkville, Victoria, Australia; Immunology and Cell Biology (1996) vol. 74, pp. 8-15.
"Committee for Veterinary Medicinal Products, Quillaia Saponins, Summary Report", The European Agency for the Evaluation of Medicinal Products, EMEA/MRL/055/95-final, Feb. 1996, pp. 1-2.
SIGMA Product Information; techserv@sial.com; Saponin From Quillaja Bark Purified; Sigma Prod. No. S4521; Case No. 8047-15-2; Oct. 25, 1996; pp. 1-3.
Sjolander, A., Bengtsson, K.L., and Morein, B., "Kinetics, Localization and Cytokine Profile of T Cell Responses to Immune Stimulating Complexes (ISCOMS) Containing Human Influenza Virus Envelope Glycoproteins," Vaccine, vol. 15, No. 9, 1997, 1030-1038.
Sjolander, A., Land, B.V., and Bengtsson, K.L., "ISCOMS Containing Purified Quillaja Saponins Upregulate both Th1-like and Th2-like Immune Responses," Cellular Immunology, 177, 1997, 69-76.
van Binnendijk et al, 1997. Protective immunity in Macaques vaccinated with live attenuated recombinant and subunit vaccines in the presence of passively acquired antibodies. "J. Infect Diseases" vol. 175, pp. 524-532.
Yifan Zhan et al., 1998, "Control of IL-12 and IFN-y Production in Response to Live or Dead Bacteria by TNF and Other Factors," The Journal of Immunology, 161, pp. 1447-1453.
Smith, R.E., Donachie, A.M., and Mcl Mowat, A., "Immune Stimulating Complexes as Mucosal Vaccines," Immunology and Cell Biology, 76, 1998, 263-269.
Karen Burke, Glynis Dunn, Morag Ferguson, Philip D. Minor, & Jeffrey W. Alamond, "Antigen Chimaeras of Poliovirus as Potential New Vaccines", Nature, vol. 332. Mar. 1988. (Abstract Only).
The European Agency for the Evaluation of Medicinal Products, Human Medicines Evaluation Unit; Committee for Proprietary Medicinal products, Note for Guidance on Pharmaceutical and Biological Aspects of Combined Vaccines; London, Jul. 23, 1998 pp. 1-14.
Rosemary E. Smith et al, 1999, "Immune-Stimulating Complexes Induce an IL-12Dependent Cascade of Innate Immune Responses," The Journal of Immunology, 162, pp. 5536-5546.
Margaretha Johansson et al. "ISCOMS with Different Quillaja Saponin Components Differ in Their Immunomodulating Activities." Vaccine, 17 (1999), pp. 2894-2900.
S. Behboudi et al. "Quillaja Saponin formulations that Stimulate Proinflammatory Cytokines Elicit a Potent Acquired Cell-Mediated Immunity." Scandinavian Journal of Immunology, 50 (1999), pp. 371-377.
Jill Ekstrom et al, "ISCOM and ISCOM-Matrix Enhance by Intranasal Route the IgA Responses to OVA and rCTB in ILocaland Remote Muscosal Secretins." Vaccine, 17 (1999) pp. 2690-2701.
Morein, B., and Bengtsson, K.L., "Immunomodulation by ISCOMS, Immune Stimulating Complexes," Methods, 19, 1999, 94-102.
Behboudi, S., Morein, B. and Villacres-Eriksson, M.C., "Quillaja Saponin Formulations that Stimulate Proinflammatory Cytokines Elicit a Potent Acquired Cell-Mediated Immunity," Scand J. Immunol., 50, 1999, 371-377.
Lars I. Nord, et al. "Novel Acetylated Triterpenoid Saponins in a Chromatographic Fraction from Quillaja Saponaria Molina." Carbohydrate Research 329, (2000), pp. 817-829.
Hu, Ke-Fei et al., Immunostimulating Complexes (ISCOMs) for Nasal Vaccination; Elsevier Science B.V. Advanced Drug Delivery Reviews 51 (2001) pp. 149-159.
Janeway, C.A., Travers, P., Walport, M.J., and Shlomchik, M.J., Immuno Biology The Immune System in Health and Disease, Garland Publishing, New York, NY, 2001, Chapter 1-Basic Concepts in Immunology, 1-34.
Janeway, C.A., Travers, P., Walport, M.J., and Shlomchik, M.J., Immuno Biology The Immune System in Health and Disease, Garland Publishing, New York, NY, 2001, Chapter 2-Innate Immunity, 35-91.
Janeway, C.A., Travers, P., Walport, M.J., and Shlomchik, M.J., Immuno Biology The Immune System in Health and Disease, Garland Publishing, New York, NY, 2001, Chapter 14-Manipulation of the Immune Response, 553-596.
Janeway, C.A., Travers, P., Walport, M.J., and Shlomchik, M.J., Immuno Biology The Immune System in Health and Disease, Garland Publishing, New York, NY, 2001, Afterword-Evolution of the Immune System: Past, Present, and Future, by Charles A.Janeway, Jr., 597-611.
www.patentstorm.us/patents/617708/description.html; Human and Marmoset Activation Viruses-US Patent 6177081, Jan. 23, 2001.
Sjolander et al. 2001. Intranasal immunisation with influenza-ISCOM induces strong mucosal as well as systemic antibody and cytotoxic T-lymphocyte. "Vaccine" vol. 19(28-29), Jul. 16, 2001, pp. 4072-4080.
Marshall, B.G., Wangoo, A., O'Gaora, P., Cook, H.T., Shaw, R.J., and Young, D.B., "Enhanced Antimycobacterial Response to Recombinant Mycobacterium bovis BCG Expressing Latency-Associated Peptide," Infection and Immunity, vol. 69, No. 11, Nov. 2001, 6676-6682.
Incorporation and live ISCOM-PubMed Results; http://www.ncbi.nlm.nih.gov/sites/entrez; Jun. 14, 2009, pp. 1-16.
ISCOM- PubMed Results; http://www.ncbi.nlm.nih.gov/sites/entrez, Jun. 14, 2009, pp. 1-3.
Incorporation and ISCOM-PubMed Results; http://www.ncbi.nIm.nih.gov/sites/entrez, Jun. 14, 2009, pp. 1-3.
Viruses, Bacterial and Fungi, Sizes and Signficance; Ion Life, http://www.ionizers.org; Jun. 16, 2009, pp. 1-4.
Vaccine Development Overview; http://www.brown.edu/Courses/Bio_160/Projects1999/vaccineoverview, Jun. 16, 2009; pp. 1-5.
Written Opinion of the International Searching Authority( Apr. 28, 2006) for PCT/SE2006/000082, publication No. WO2006/078213 A1, published Jul. 27, 2006.
International Search Report (Apr. 28, 2006) for PCT/SE2006/00082, publication No. WO2006/078213 A1 published Jul. 27, 2006.

Iosef, et al., Systemic and Intestinal Antibody Screening Cell Responses and Protection in Gnotobiotic Pigs Immunized Orally With Attenuated . . . , Vaccine 20 (2002) 1741-1753.

Francis, George, et al., The Biological Action of Saponins in Animal Systems: A Review; British Journal of Nutrition (2002), vol. 88, pp. 587-506; The Authors 2002.

Sittelaar et al. 2002, Longevity of neutralizing antibody levels in macaques vaccinated with Quil A-adjuvanted measles vaccine candidates. "Vaccine" vol. 21(3-4), Dec. 13, 2002, pp. 155-157, Available online Sep. 27, 2002.

Maria S. Di Genaro et al., Apr. 2003, "Attenuated Yersinia enterocolitica Mutant Strains Exhibit Differential Virulence in Cytokine-Deficient Mice: Implications for the Development of Novel Live Carrier Vaccines," Infection and Immunity, American Society of Microbiology, vol. 71, Issue 4, pp. 1804-1812.
Ed C. Lavelle et al., "Cholera Toxin Promotes the Induction of Regulatory T Calss Specific for Bystanders Antigens by Modulating Dendritic Cell Activation." The Journal of Immunology, (Sep. 2003), 171: 2384-2392.
International Search Report for PCT/SE2003/01180 dated Sep. 10, 2003.
BCCDC Laboratory Services; A Guide to Selection and Use of Disinfectancts; BC Centre for Disease Control 2003, pp. 1-18.
Bror Morein et al., "Current Status and Potential Application of ISCOMs in Veterinary Medicine." Advance Drug Delivery Reviews, 56 (Jun. 2004), pp. 1367-1382.
Sparg, S.G., et al., Biological Activities and Distribution of Plant Saponins; Journal of Ethno-Pharmacology; www.elsevier.com/locate/jethpharm; vol. 94 (Oct. 2004), pp. 219-243.
Written Opinion of ISA PCT/SE2004/001038 dated Jan. 11, 2004.
International Search Report PCT/SE2004/001038 dated Jan. 11, 2004.
Mooij, P., Nieuwenhuis, I.G., Knoop, C.J., Doms, R.W., Bogers, W.M.J.M., Haaft, P.J.F., Niphuis, H. Koornstra W., Bieler, K., Kostler, J., Morein, B., Cafaro, A., Ensoli, B., Wagner, R., and Heeney, J.L., "Qualitative T-Helper Responses to Multiple Viral Antigens Correlate with Vaccine-Induced Immunity to Simian/Human Immunodeficiency Virus Infection," Journal of Virology, vol. 78, No. 7, Apr. 2004, 3333-3342.
Harold F. Stills, Jr., 2005, "Adjuvants and Antibody Production: Dispelling the Myths Associated with Freund's complete and Other Adjuvants," ILAR Journal, vol. 46, Issue 3, pp. 280-293.
The European Medicines Agency, Evaluation of Medicines for Human Use; Committee for Medicinal Products for Human Use, Guidelines on Adjuvants in Vaccines for Human Use; London, Jan. 20, 2005 pp. 1-18.
Debbie Drane et al., "Iscomatrix Adjuvant for Prophylactic and Therapeutic Vaccines." Experts Rev. Vaccines, 6(5), (Oct. 2007), pp. 761-772.
Jim E. Eyles et al., "Immunodominant Francisella Tularensis Antigens Identified Using Proteome Microarray." Proteomics, Jun. 2007, pp. 2172-2183.
Roner, Michael R., et al., Antiviral Activity Obtained from Aqueous Extracts of the Chilean Soapbark Tree (Quilaja Saponaria Molina); Journal of General Virology, Jan. 2007, vol. 88, pp. 275-285.
Rajput, Zahid Iqbal et al., Adjuvant Effects of Saponins on Animal Immune Responses; Journal of Zhejiang University Science B, Mar. 2007 vol. 8 (3) pp. 153-161.
Initiative for Vaccine Research, Live Attenuated Vaccines; World Health Organization, Jun. 2009, p. 1.

* cited by examiner

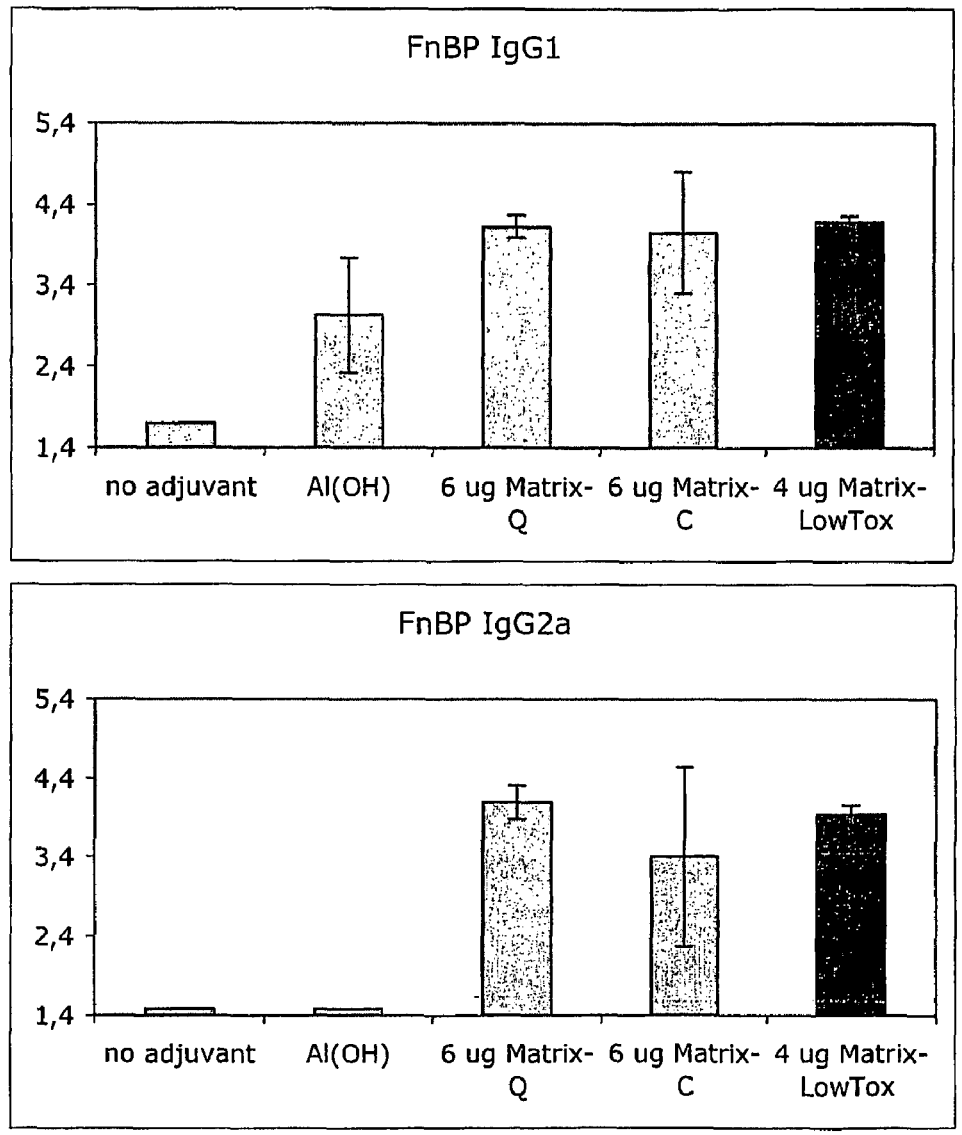
Fig 1:1
Serum antibody responses to Fibronectin binding protein (FnBP) after the second immunization with FnBP in various adjuvant formulations

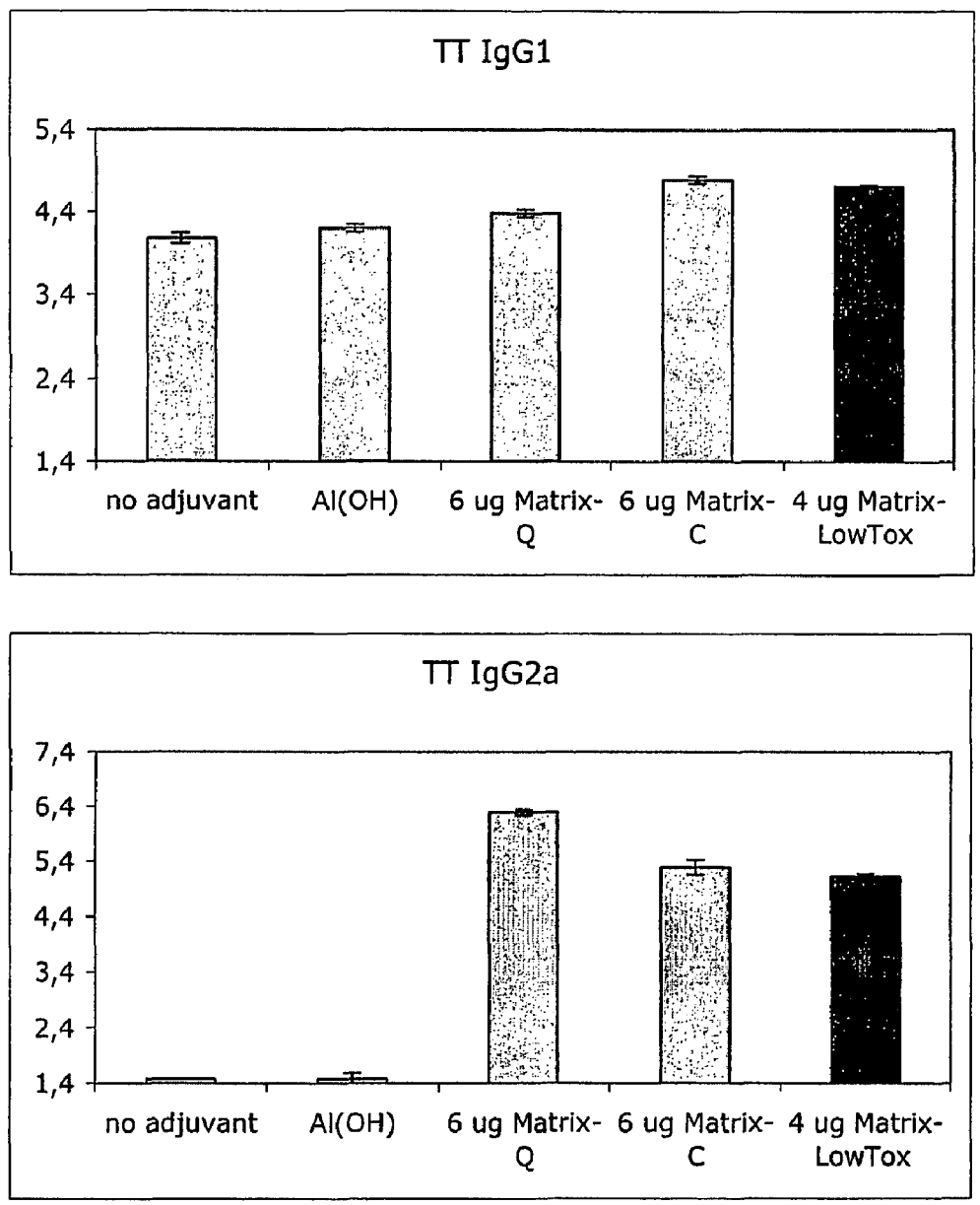
Fig 2:1
Serum antibody responses to Tetanus Toxoid (TT) after the second immunization with TT in various adjuvant formulations

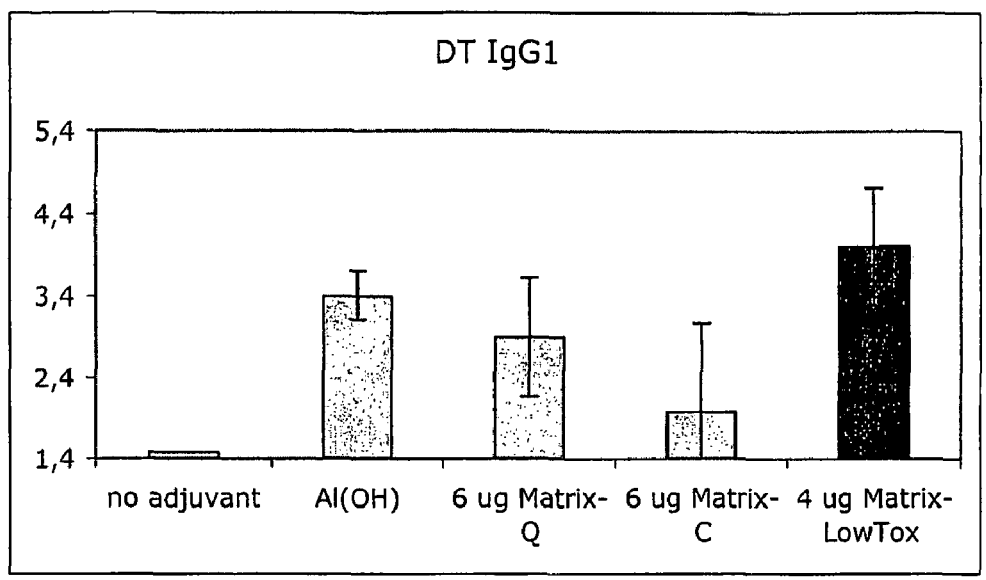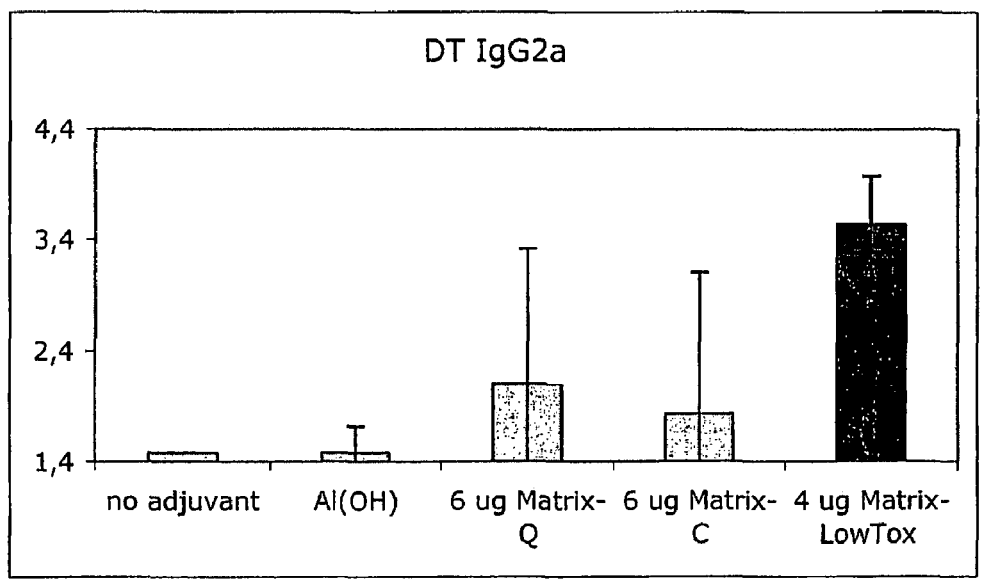
Fig 3:1
Serum antibody responses to Diptheria Toxoid (DT) after the second immunization with DT in various adjuvant formulations

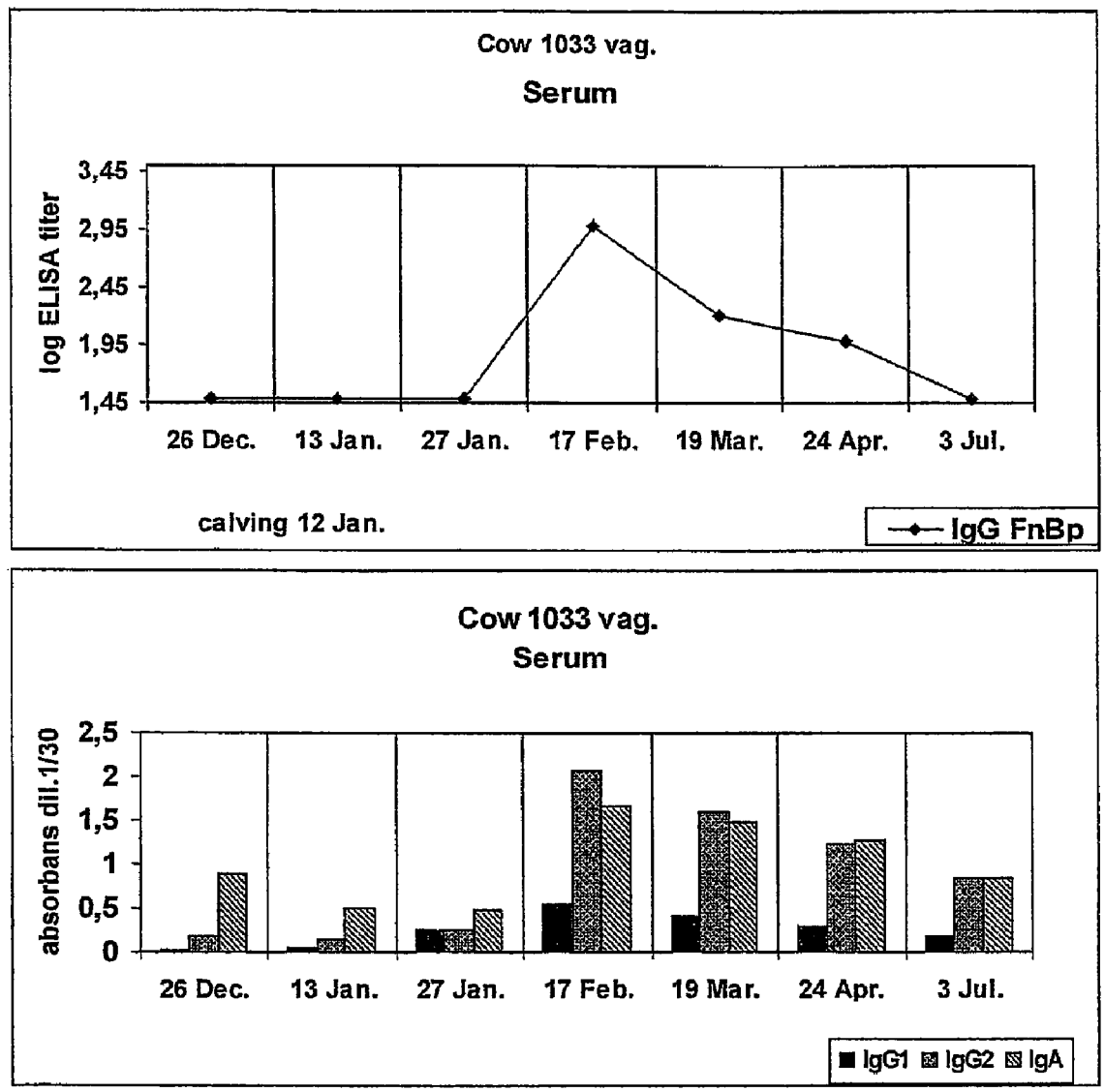
Fig. 4:1A

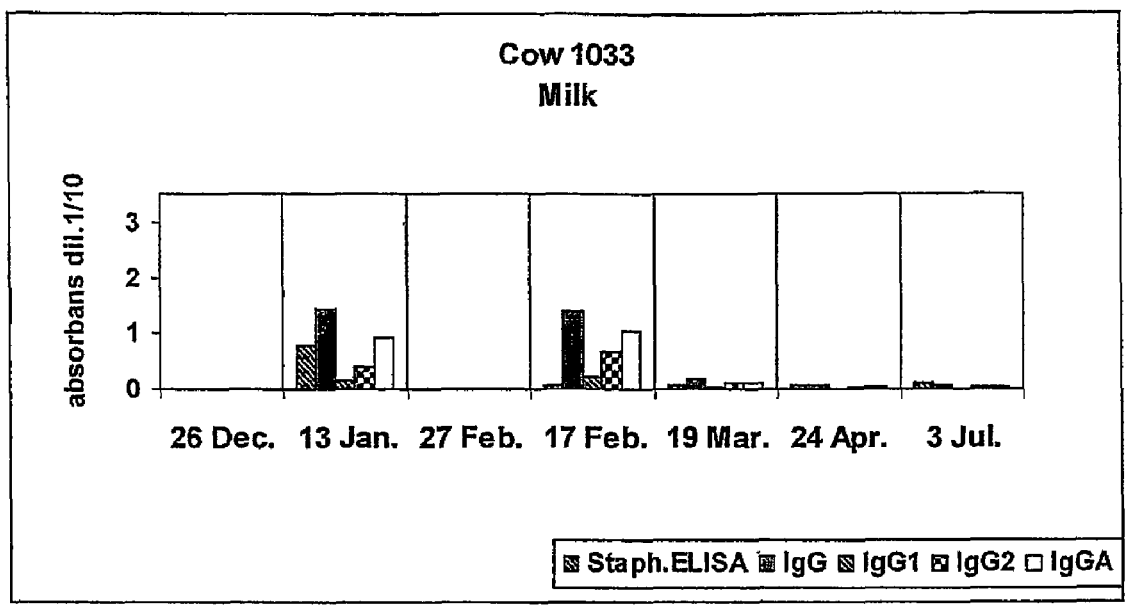
Fig. 4:1B
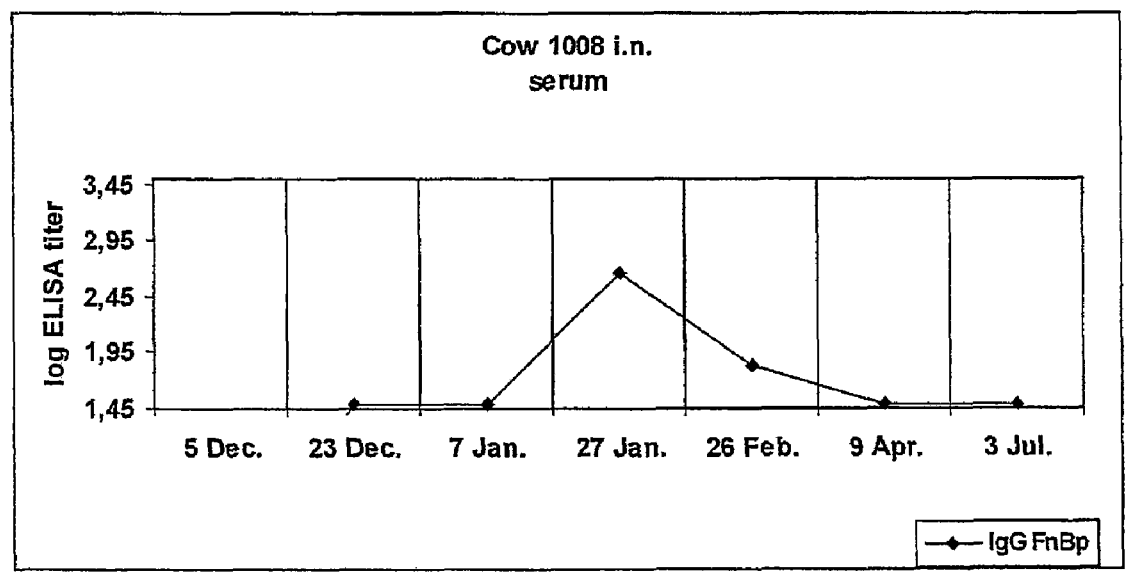
Fig. 4:2A

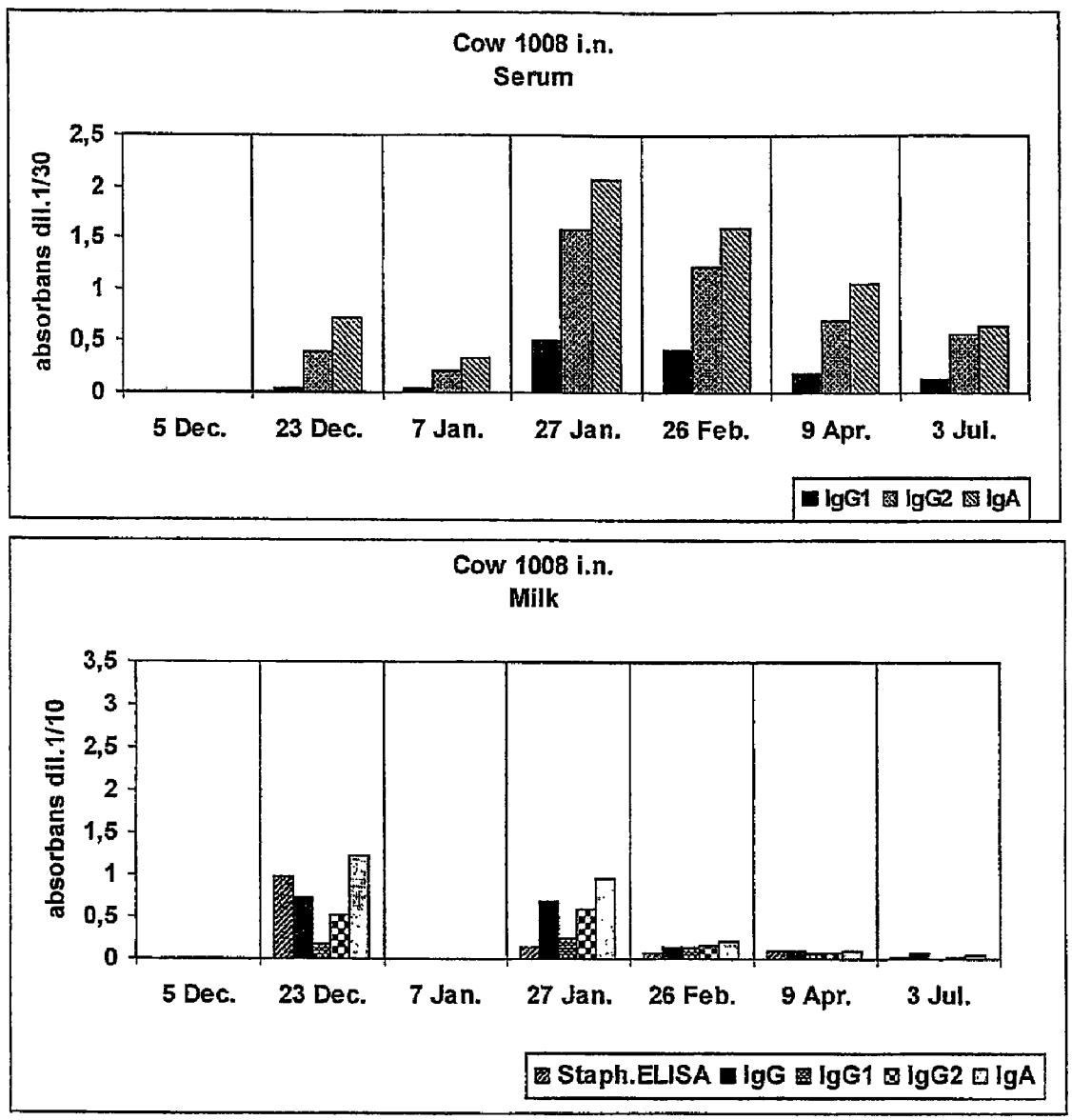
Fig 4:2B

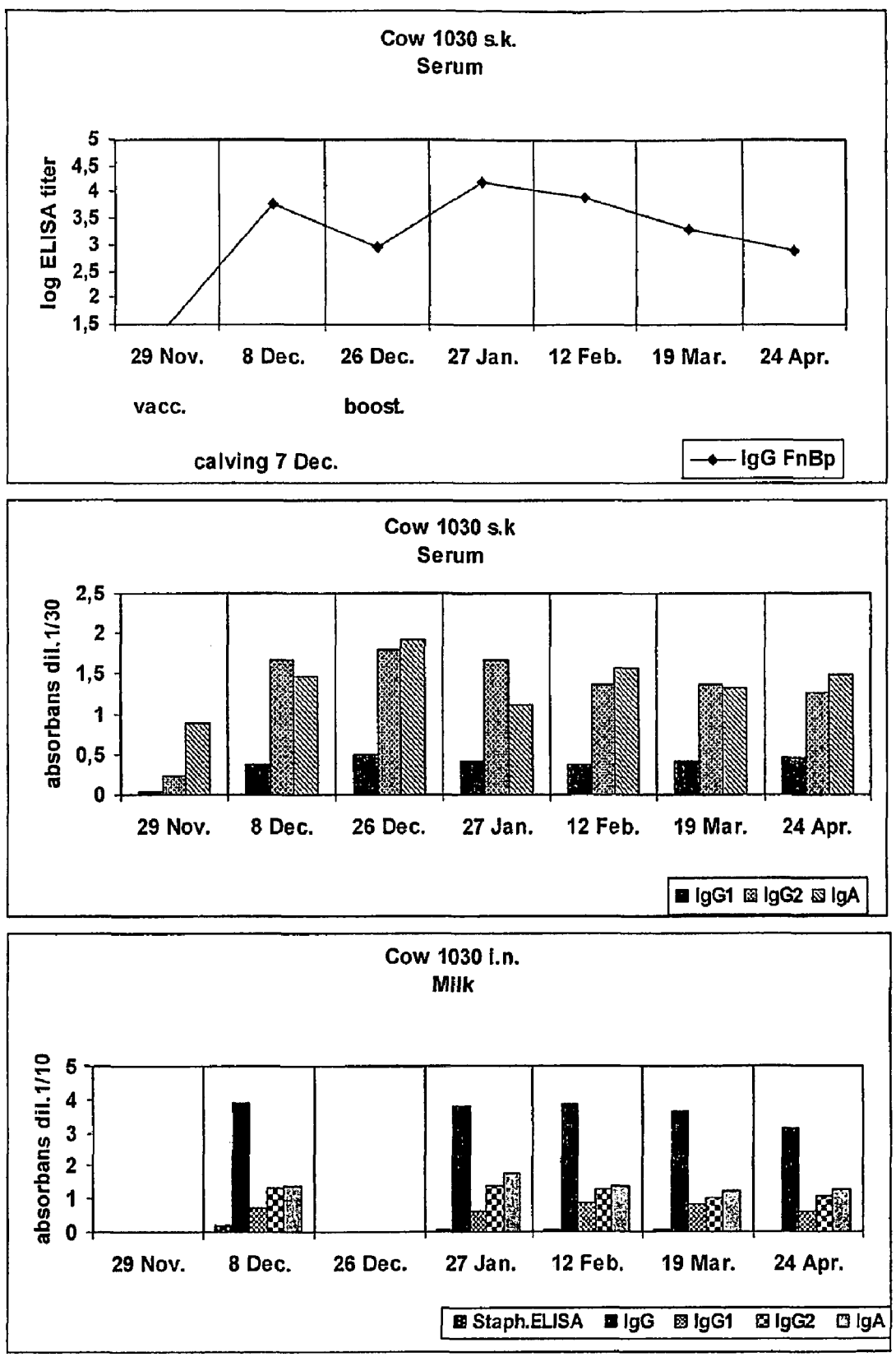
Fig 4:3

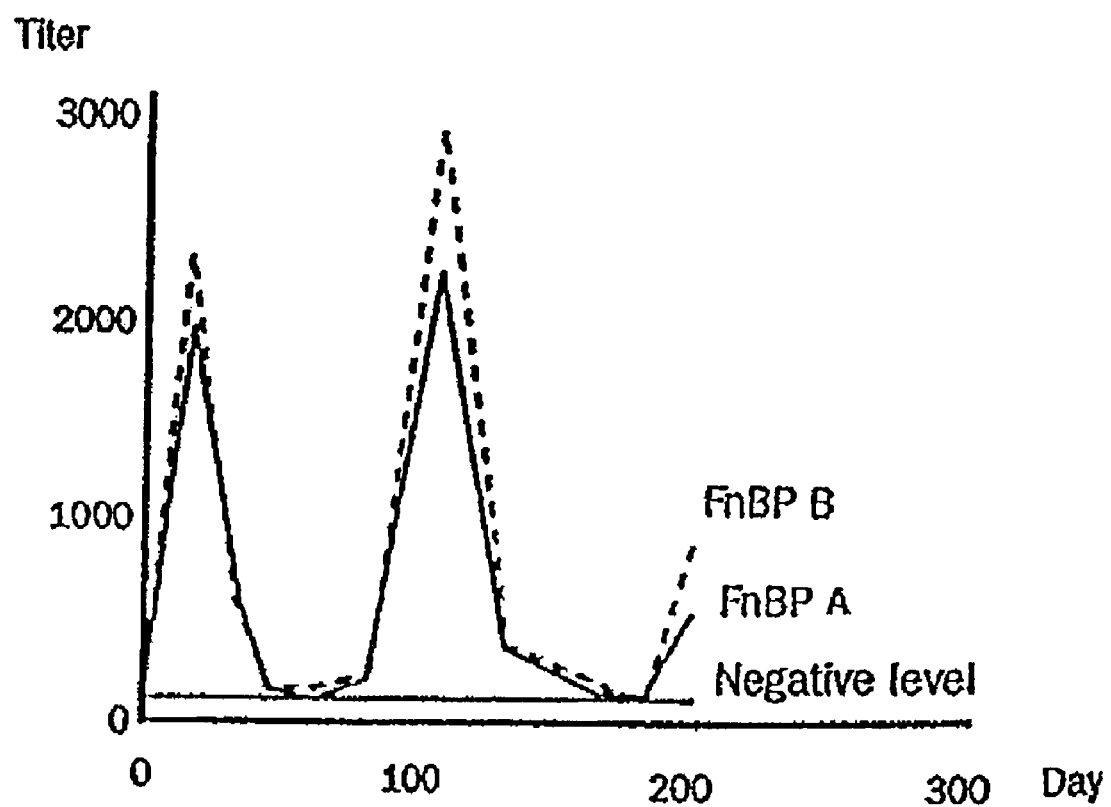
Fig 4:4

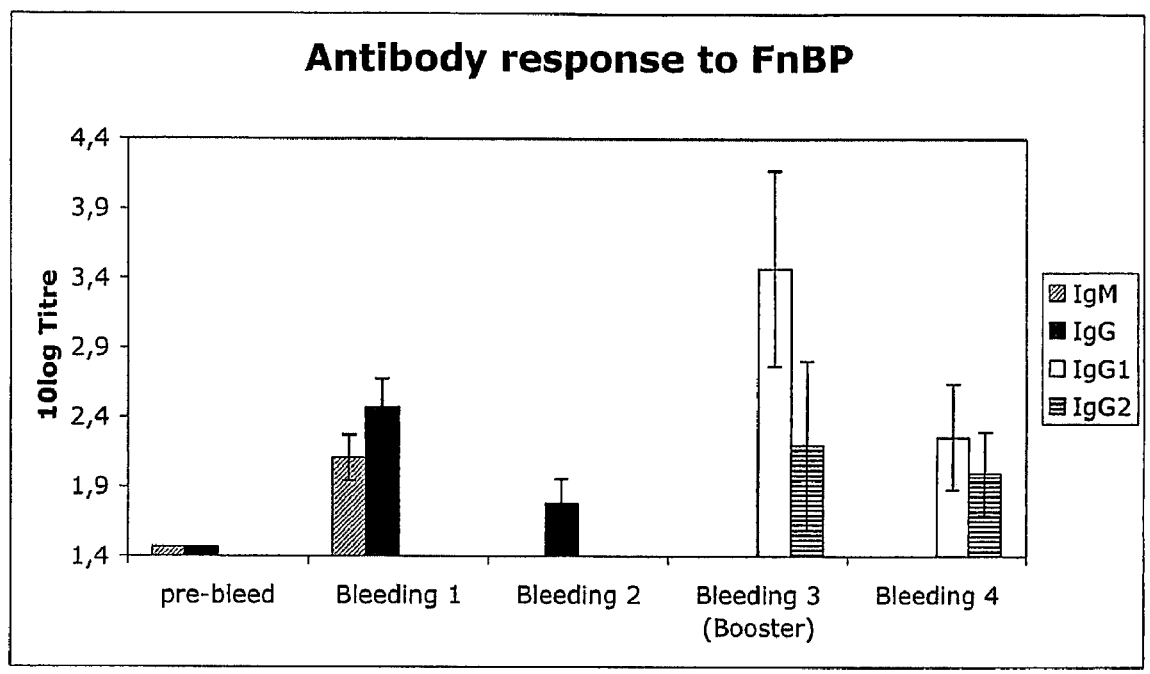
Figure 5:1

A
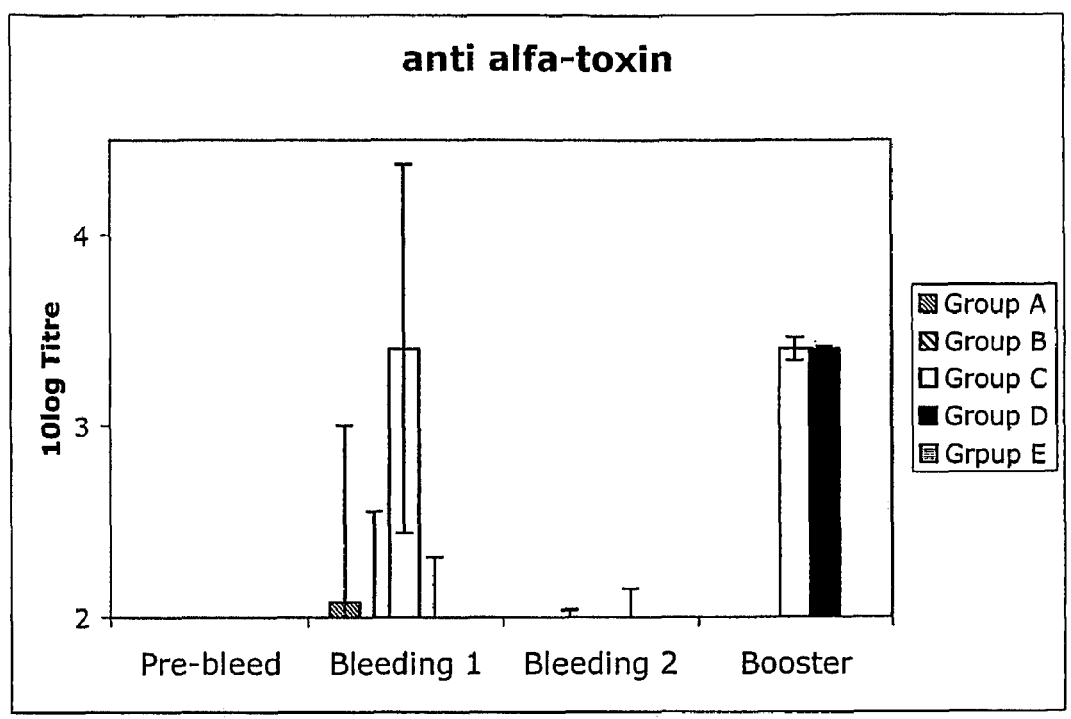
B
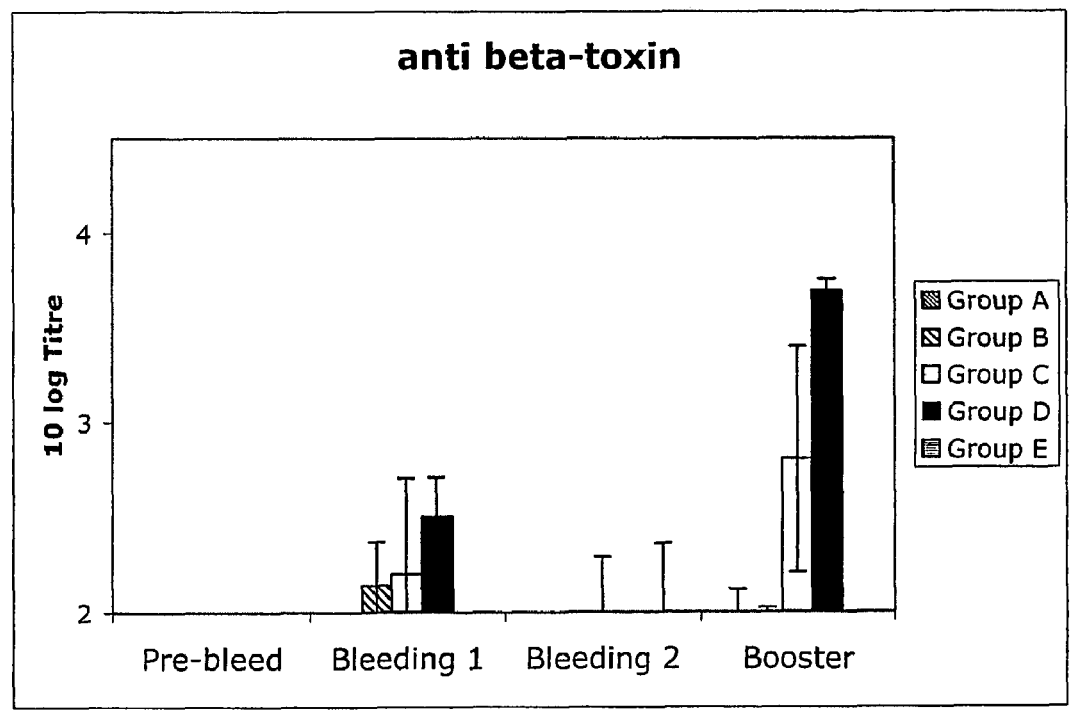
Figure 5.2

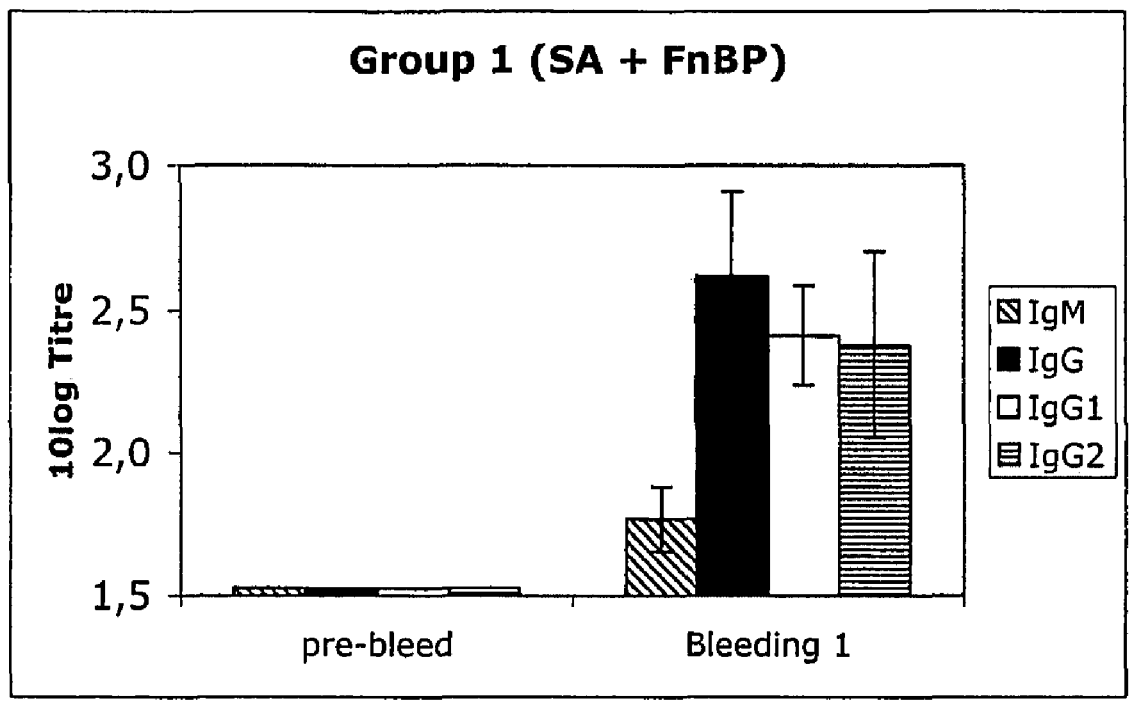
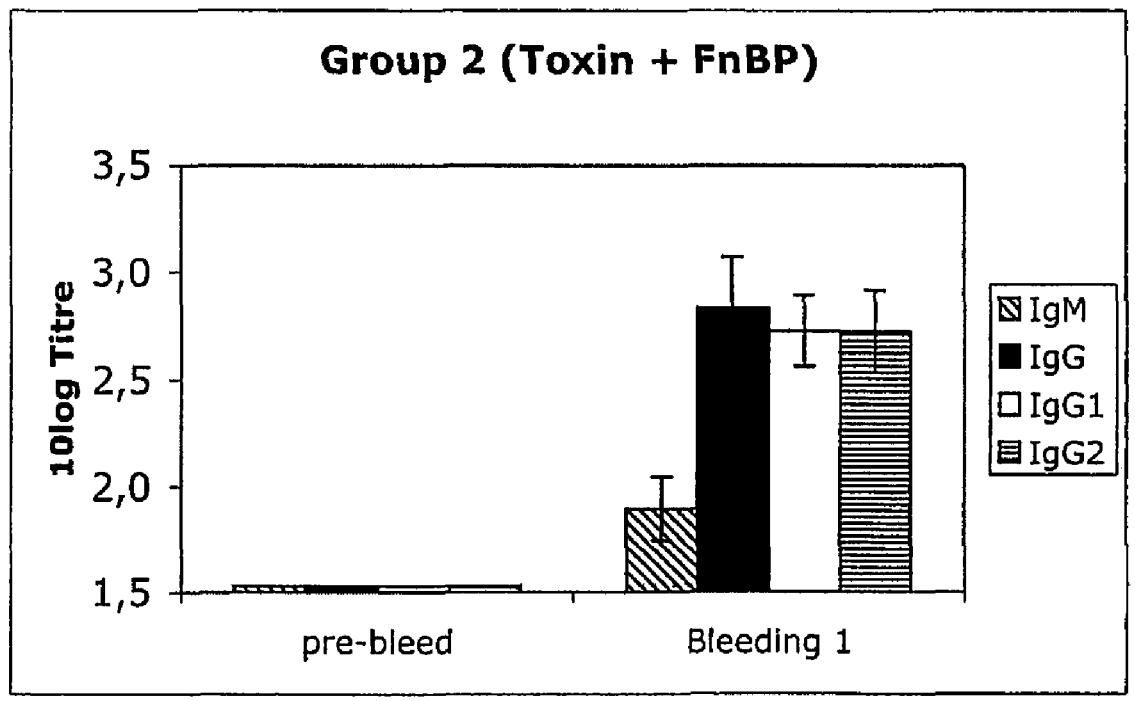
Figure 6

VACCINE COMPOSITION COMPRISING A FIBRONECTIN BINDING PROTEIN OR A FIBRONECTIN BINDING PEPTIDE

RELATED APPLICATIONS

This application is a nationalization under 35 U.S.C. 371 of PCT/SE2006/000082, filed Jan. 20, 2006 and published as WO 2006/078213 A1 on Jul. 27, 2006, which claimed priority under 35 U.S.C. 119(e) to U.S. Provisional Patent Application Ser. No. 60/593,504, filed Jan. 20, 2005; which applications and publication are incorporated herein by reference and made a part hereof.

The present invention relates to a composition comprising at least one fibronectin binding protein, and/or at least one a truncated fibronectin binding protein and/or at least one fibronectin binding peptide, all comprising at least one fibronectin binding domain; and at least one iscom matrix complex and/or liposome and/or at least one lipid and at least one saponin, whereby the at least one lipid and the at least one saponin may be in complex, solution or suspension.

Further, the invention also relates to use thereof for the preparation of a vaccine against a micro organism that comprises at least one fibronectin binding domain. It also regards a kit of parts comprising at least two compartments, wherein one compartment comprises at least one truncated fibronectin binding protein and/or a fibronectin binding peptide, that comprises at least one fibronectin binding domain, and another compartment comprises an instruction for use and/or an iscom matrix complex and/or an iscom complex and or a liposome. Further it relates to a method for vaccination of an animal.

TECHNICAL BACKGROUND

SA is a pathogen, which causes diseases in virtually all mammalian species. SA is an important pathogen in the bovine, ovine and caprine species causing suffering and very high economical losses in the dairy breeds including cattle, sheep and goats (cattle) all over the world. The SA induced mastitis might be the single most important economical negative factor in veterinary medicine due to the pathogenicity including severe acute and painful inflammation, chronic and persistent conditions and the difficulties with efficient treatments mostly based on antibiotics that might not work because of the resistance leading culling. The alternative would be vaccination, but no efficient vaccine so far exists, which can constitute the basis for combating the mastitis problem caused by SA.

There are several pathogenicity factors for a prospective protective vaccine against SA infections to overcome. E.g. SA "hides" antigens in the cell essential for the infection and for its survival. Further SA has the capacity to manipulate the host immune system to facilitate the bacterial existents. This complex situation is one reason that an efficient SA vaccine for protection against mastitis is not available.

SA components that manipulate and may down regulate the immune response of the host that includes excreted products such as α- and β-toxins, leukocidin. Also cell bound components like super antigens and protein A is involved.

Examples of essential structures that the bacteria hide for the immune system of the host it infects is Fibronectin binding proteins (FnBp) or external fibrin factor (Ebf) essential for adherence of SA to tissue e.g. in wounds.

Several Fibronectin binding microbial surface components-recognizing adhesive matrixmolecules have been isolated and characterized from different Gram-positive bacteria. Genes encoding Fibronectin binding microbial surface components recognizing adhesive matrixmolecules from *Staphylococcus aureus* (Signas et al., "Nucleoside sequence of the gene for a fibronectin binding protein from *Staphylococcus aureus*: Use of this peptide sequence in synthesis of biologically active peptides," Proc. Natl. Acad. Sci. USA. 86:699-173, 1989.), *Streptococcus pyogenes* (Talay et al., "Fibronectin-binding protein of *Streptococcus pyogenes*: Sequence of the binding domain involved in adherence of streptococci to epithelial cells," Infect. Immun., 60:3837-3844, 1992.; Hansky et al., Infect. Immun., 60:5119-5125, 1992) and *Streptococcus dysgalactiae* (Lindgren et al., "Two different genes coding for fibronectin-binding proteins from *Streptococcus dysgalactiae*—the complete nucleotide sequences and characterization of the binding domains," Eur. J. Biochem., 214:819-827, 1993.) have been cloned and sequenced. The deduced amino acid sequences revealed 60-100 kDa proteins with very similar structural organization. The N-terminal signal sequence is followed by a long stretch of unique sequence, which in some cases is interrupted by two copies of an approximately 30 amino acid long segment. The ligand binding site is located just N-terminal of a proline-rich domain, which is believed to anchor the proteins in the cell wall. This domain is followed by the sequence LPXTGX which is a cell wall targeting signal (Schneewind et al., Science, 268:103-106, 1995. et al., 1995), a stretch of hydrophobic residues representing a trans-membrane unit and a short C-terminal cytoplasmic domain containing a cluster of positively charged residues. *Streptococcus agalactiae* and *Streptococcus uberis* and coagulase negative *Staphylococcus*, have similar fibronectin binding devices and are of special interest for mastitis in the bovine and ovine species. Also coagulase negative *Staphylococci* have FnBp and are causing mastitis. The primary Fibronectin binding sites on these microbial surface components recognizing adhesive matrix molecules consist of 30-42 amino acid long motifs repeated 3-4 times, and most of the repeated units contain a consensus sequence (Lindgren et al., 1993 loc cit; McGavin et al., "Fibronectin receptors from *Streptococcus dysgalactiae* and *Staphylococcus aureus*: Involvement of conserved residues in ligand binding," J. Biol. Chem. 268:23946-23953, 1993.). This domain is composed of a unit of 37-40 amino acids, repeated three or four times (FIG. 1 of U.S. Pat. No. 6,685,943).

Thus, FnBp is an important adhesion protein (antigen) for the formulation a protective vaccine against several gram-positive bacteria including SA based on the function of adhesion and even more as a target for phagocytosis being the main protective mechanism against SA. Importantly, FnBp is present in many isolates from gram-positive bacteria such as *Streptococcus pyogenes* and/or *Streptococcus dysgalactiae* and *Streptococcus agalactiae* and *Streptococcus uberis* and coagulase negative *Staphylococcus*, and coagulase negative *Staphylococcus*. Close to 100% of SA isolates. A vaccine would not only be for protection of cows against mastitis caused by SA infection, but also for virtually all animal species affected by infections caused by SA including man.

The composition of vaccine antigens might vary in vaccines against gram-positive bacteria, including SA infections and SA caused disease depending on several factors including local strains and clinical pictures. The adhesion to fibronectin mediates an important and common factor for the infection process, and this protein is present on virtually all SA isolates. The blocking of adhesion and neutralisation is an effect by IgG1 by antibodies, while IgG2a is important for phagocytosis the major immune protective mechanism against SA.

In view of the fact that SA also is an intracellular parasite the cell mediated arm of the immune system (CMI) is an essential factor. It is well documented that the iscom system potently enhances CMI and in particular the cytotoxic T cells killing infected cells e.g. SA infected cells. Thus, the adjuvant formulations based on the iscom-technology have the capacity to evoke several immune protective mechanisms.

Iscoms containing FnBp have been reported (Nickerson Nelson et al. 2000 (Symposium, Stresa Italy, Proceedings, 426-4319). A FnBp was incorporated into the iscom matrix to form an iscom with integrated antigen. Nelson's iscom formulation was however not sufficiently immunogenic and not useful for vaccines partly because of the short duration of immunity it induced. The present invention based on iscom matrixor liposomes as adjuvant gives a far better immunity (see present example 5 for comparison). Further, the vaccine formulation according to this invention is much better suited for large-scale production, since the iscom technology used in this invention only requires the addition of iscom matrix to the vaccine antigen suspension.

It has now turned out that the iscom technology is very well suited for preparation of vaccine compositions against gram-positive bacteria, including *Staphylococcus aureus* SA and especially against mastitis in the bovine species.

SUMMARY OF THE INVENTION

The present invention relates to a composition comprising at least one fibronectin binding protein, and/or at least one a truncated fibronectin binding protein and/or at least one fibronectin binding peptide, all comprising at least one fibronectin binding domain; and at least one iscom matrix complex and/or liposome and/or at least one lipid and at least one saponin, whereby the at least one lipid and the at least one saponin may be in complex, solution or suspension.

Further, it relates to the use thereof for the preparation of a vaccine against a micro organism that comprises at least one fibronectin binding domain. It also regards a kit of parts comprising at least two compartments, wherein one compartment comprises at least one truncated fibronectin binding protein and/or a fibronectin binding peptide, that comprises at least one fibronectin binding domain, and another compartment comprises an instruction for use and/or an iscom matrix complex and/or an iscom complex and or a liposome. Further it relates to a method for vaccination of an individual.

The invention is elucidated by way of the following tables and figures:

Table 1:1

Lay out of the immunization of Balb/C mice with fibronectin binding protein (FnBp). The mice were immunized twice s.c. four weeks apart with the respective vaccine candidates Table 2:1

Lay out of the immunization of Balb/C mice tetanus toxoid (TT). The mice were immunized twice s.c four weeks apart with the respective vaccine candidates Table 3:1

Lay out of the immunization of Balb/C mice with difteri toxoid (DT). The mice were immunized twice s.c. four weeks apart with the respective vaccine candidates Table 3:1

Lay out of the immunization of Balb/C mice with difteri toxoid (DT). The mice were immunized twice s.c. four weeks apart with the respective vaccine candidates

FIG. 1:1

Serum antibody responses in IgG1 and IgG2 subclasses to Fibronectin binding protein (FnBp) after the second immunization of Balb/C mice with FnBp in various adjuvant formulations

FIG. 2:1

Serum antibody responses to Tetanus Toxoid (TT) after the second immunization of Balb/C with TT in various adjuvant formulations measured in IgG1 and IgG2 subclasses.

FIG. 3:1

Serum antibody responses in IgG1 and IgG2 subclasses to Diptheria Toxoid (DT) after the second immunization of Balb/C with DT in various adjuvant formulations FIGS. 4:1 through 4:4

Ten heifers were primed with FnBp adjuvanted with iscom matrix before going into lactation by intra vaginal (ivag) route (4:1) 1 animal out of 3 is shown; or by intra-nasal (i.n.) priming (4:2) 1 animal out of 3 is shown, or by s.c. administration (4:3) 1 animal out of 4 is shown. The second immunisation was for all groups carried out s.c. three to four weeks later and after that the lactation period had commenced. The antibody responses were analysed in serum and milk whey by ELISA by measuring the total total Ig, IgG1, IgG2 and IgA as depicted in the figures.

FIG. 5:1

The antibody responses to fibronectin binding protein (FnBp) of five calves 4 to 7 months old vaccinated with FnBp adjuvanted with iscom matrix twice 6 weeks apart. The immune responses after the first immunization are recorded in the IgM and total IgG classes. After the second immunization the antibody responses are recorded in the IgG1 and IgG2 subclasses.

FIG. 5:2

The antibody responses to α (A) and β (B) toxins of 4 to 7 months old calves vaccinated twice six weeks apart with various formulations (see below). The antibody responses were measured by toxin neutralization tests.

Five calves in each group were immunized with:

Group A: FnBp adjuvanted with iscom matrix

Group B: FnBp plus *Staphylococcus aureus* (SA) and α and β toxins and adjuvanted with iscom matrix at the first immunization thereafter with FnBp only Group C: FnBp with SA and plus α and β toxins and adjuvanted with iscom matrix at both immunizations Group D: SA and α and β toxins and adjuvanted with iscom matrix at both immunizations Group E: Non-immunized controls

FIG. 6

The antibody responses of calves in the age of 1 to 2 years old vaccinated ones with fibronectin binding protein (FnBp) supplemented with *Staphylococcus aureus* (A) cells or α and β toxins (B). The experimental vaccines were adjuvanted with iscom matrix. The antibody responses were measured in the IgM, total IgG, IgG1 and IgG2 classes and subclasses.

DETAILED DESCRIPTION OF THE INVENTION

The invention relates to a composition comprising at least one fibronectin binding protein (FnBp), and/or at least one a truncated fibronectin binding protein and/or at least one fibronectin binding peptide that comprises at least one fibronectin binding domain, and at least one iscom matrix complex and/or liposome and and/or at least one lipid and at least one saponin, whereby the at least one lipid and the at least one saponin may be in complex, solution or suspension.

The composition may be used for preparing vaccine against gram-positive bacteria such as *Staphylococcus*

*aureus, Streptococcus pyogenes, Streptococcus dysgalactiae Streptococcus agalactiae* and *Streptococcus uberis* and coagulase negative *Staphylococcus*.

A full length fibronectin binding protein may be used as well as a truncated protein or peptide as long as it comprises at least one fibronectin binding domain or epitope. By truncated protein we understand a naturally occurring or synthetically produced full length protein from which one or more amino acids have been deleted. One ore more of the amino acids in the non FnBp binding regions may be deleted. Amino acids from the FnBp binding may also be deleted. However, at least one FnBp binding domain or epitope should rest unaffected.

Preferably the truncated protein or peptide comprise one ore fibronectin binding domains from a gram-positive bacteria, especially from *Staphylococcus aureus, Streptococcus pyogenes, Streptococcus dysgalactiae Streptococcus agalactiae* and *Streptococcus uberis* and coagulase negative *Staphylococcus*

The fibronection binding domain may be selected from the D domains from fibronectin binding protein A or B from *Staphylococcus aureus*, such as the DU and D1-D4 domains; the A domains from fibronectin binding protein A from *Streptococcus dysgalactiae*, such as the AU and A1-A3 domains; the B domains from fibronectin binding protein B from *Streptococcus dysgalactiae*, such as the B1-B3 domains; and the domains from fibronectin binding protein *Streptococcus pyogenes* such as the P1-P4 domains (see FIG. 1 of U.S. Pat. No. 6,685,943). FnBp binding domains of *Staphylococcus aureus* are also described in Signäs et al.: (1989) Nucleotide sequence of the gene fibronectin-binding protein from *Staphylococcus aureus*: Use of this peptide sequence in the synthesis of biologically active peptides. *Proc. Natl. Acad. Sci. USA*, Vol:86 pp. 699-703.

The truncated protein or peptide may comprise 1-200, preferably 1-100 such as 1-50, such as 1-20 amino acids up stream or down stream of one or more of the FnBp binding domains e.g. the D, A, P domains mentioned above.

The truncated protein and the peptide may be a naturally occurring amino acid sequence or be synthetically produced, or produced by hybrid DNA technology. One ore more of these FnBp binding domains or several repeating units comprising one or more of the above mentioned FnBp binding domains may be produced and used according to the invention.

How to obtain naturally occurring and synthetically produced FnBp binding domains are generally described in U.S. Pat. No. 6,685,943

The identification of Fn-binding domains or epitopes is generally known in the art. For example, one may employ the methods of Hopp, as taught in U.S. Pat. No. 4,554,101, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

In general, the size of the domain or epitope is not particularly crucial, so long as it is at least large enough to bind to FnBp. The smallest useful core sequence expected by the present disclosure is generally on the order of about at least 5 amino acids in length, with sequences on the order of 10 or 50 being more preferred. One or more FnBp domains or epitopes may be used.

The identification of epitopic core sequences is known to those of skill in the art, for example, as described in U.S. Pat. No. 4,554,101 which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g, DNAStar 7 software, DNAStar, Inc., Madison, Wis.) may also be useful in designing synthetic FnBps, and FnBp-derived epitopes and epitope analogs in accordance with the present disclosure.

In this regard, particular advantages may be realized through the preparation of synthetic peptides that include epitopic/immunogenic-core sequences. These epitopic core sequences may be identified as hydrophilic and/or mobile regions of the polypeptides or those that include a T cell motif.

To confirm that a protein or peptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as the FnBp-derived peptide, or a known antibody, will be labelled with a detectable label and the test components, that generally remain unlabeled, will be tested for their ability to reduce the amount of label that is bound to the corresponding reactive antibody or antigen.

Useful peptides for use according to the invention may be obtained as described in the examples, general information before example 1 and in example 1.

In order to better purify the truncated protein or peptide these may be produced by DNA engineering and a sequence inserted coding for an amino acid sequence having affinity for materials that may be used for separation. For example one may introduce 6 histidine; one or more positive amino acids; and/or the zz(z) region from protein A that bind to a chelating (Ni- or Co-) material; an ion exchange material and immuno affinity material respectively. Such methods are generally known in the art.

The fibronectin binding protein, the truncated fibronectin binding protein and the fibronectin binding peptide that comprises at least one fibronectin binding domain may be isolated from the bacterial cell of any of the above mentioned bacteria. The may also be isolated from excreted products from the bacteria.

Further the antigens may be produced as rDNA products from bacterial cells; fungal or from mammalian cells according to known technology.

They may also be produced in vector systems; or in vivo after immunization with so called DNA vaccines or be produced as so called RNA vaccines as is generally known in the art.

They may also be produced as fusion proteins and be e.g. rDNA products from bacterial cells; be produced as fusion proteins and be rDNA products from fungal cells; be produced as fusion proteins and be rDNA products from mammalian cells; or produced as fusion proteins in vector systems from bacterial cells; produced as fusion proteins in vector systems from fungal cells; produced as fusion proteins in vector systems from mammalian cells.

Further, the fusion product may be a conjugate between a protein and a carbohydrate capsular antigen from a gram-positive bacteria such as *Staphylococcus aureus, Streptococcus pyogenes, Streptococcus dysgalactiae Streptococcus agalactiae* and *Streptococcus uberis* and coagulase negative *Staphylococcus*, or the fusion protein product may be a conjugate between two proteins where at least one of the proteins is a bacterial protein from any of the above mentioned micro organisms such as a *Staphylococcus aureus* protein.

The fibronectin binding protein and/or the truncated fibronectin binding protein and/or fibronectin binding peptide may be integrated into liposomes or mixed with iscom matrixor liposomes or coupled on liposomes or iscom matrix.

The iscom matrix complex in the compositions of the invention comprises at least one glycoside and at least one lipid. The lipid is at least a sterol such as cholesterol and optionally also phosphatidyl choline matrix has an immunoenhancing effect on co-administered antigenic substances, see EP 0 436 620 B1 and may be produced as described in this patent.

The composition iscom, the matrix complexes and/or the liposomes, may also contain one or more other immuno-modulatory (adjuvant-active) substances, not necessarily a saponin, e.g. lipopolysacharides (LPS), Lipid A or Lipid A derivatives, CT or LT and their sub-fragments or derivatives thereof e.g., LTB, LTA, CTB, CTA or CTA1-DD The iscom matrix may be one or more iscom matrix particles or any sub-fragment(s) of the 6 nanometer rings thereof. Any mixtures of such iscom matrix, particles or sub fragments may be used. One or more antigens may be used and a transport and passenger antigen may be used as described in EP 9600647-3 (PCT/SE97/00289).

The lipids used are particularly those described in the applicant's patent EP 0 109 942 B1 in particular on p. 3 and in patent EP 0 436 620 B1 on p. 7 lines 7-24. Especially sterols such as cholesterol and phospholipids such as phosphatidyle-thanolamin and phosphatidylcolin are used. Lipid-containing receptors that bind to the cell-binding components, such as glycolipids including the cholera toxin's receptor, which is the ganglioside GM1, and fucosed blood group antigen may be used. The cell-binding components can then function as mucus targeting molecule and be bound to the lipid-containing substances through simply mixing them with complexes that contain them. Iscom complexes comprising such receptors and receptors are described in WO 97/30728.

Useful glycosides are described in EP 0 109 924 B1. Saponins and triterpensaponins are preferred. The may be in the form of raw extract from *Quillaja Saponaria* Molina" (Dalsgaard, K. (1974), Arch. Gesamte Virusforsch, 44, 243.), or any sub-fraction thereof as described in PCT/US/88101842 to Kensil et al., Kensil, C. A. et al. (1991), J. Immunol., 146, 431, Kersten, G. F. A. et al. (1990). "Aspects of Iscoms. Analytical, Pharmaceutical and Adjuvant Properties; Thesis, University of Utrecht, EP 0 362279B2 and EP 0555 276B1.

According to one aspect of the invention the iscom matrix complex comprises crude or raw extract of Quil A comprising a mixture of saponines or a semipurified form thereof such as Quillaja Powder Extract (Berghausen, USA), Quillaja Ultra Powder QP UF 300, Quillaja Ultra Powder QP UF 1000 or Vax-Sap (all three from Natural Responses, Chile).

According to another aspect of the invention the iscom matrix complex comprises at least one purified glycoside such as a saponin fraction from Quil A.

The purified saponin fractions according to the invention may be the A, B and C fractions described in WO 96/11711, the B3, B4 and B4b fractions described in EP 0 436 620 The fractions QA1-22 described in EP 0 3632 279 B2, Q-VAC (Nor-Feed, AS Denmark), *Quillaja Saponaria* Molina Spikoside (Isconova AB, Uppsala Science Park, 751 83, Uppsala, Sweden).

The fractions QA-1-2-3-4-5-6-7-8-9-10-11-12-13-14-15-16-17-18-19-20-21 and 22 of EP 0 3632 279 B2, Especially QA-7, 17-18 and 21 may be used. They are obtained as described in EP 0 3632 279 B2, especially at page 6 and in Example 1 on page 8 and 9. Preferably sub fractions A and C are used.

The term "one saponin fraction from *Quillaja Saponaria* Molina." is used throughout this specification and in the claims as a generic description of a purified or defined saponin fraction of *Quillaja Saponaria* or a substantially pure fraction. It is important that the fraction does not contain as much of any other fraction to negatively affect the good results that are obtained when the mixtures of iscom or iscom matrix comprising essentially one fraction is used. The saponin preparation may, if desired, include minor amounts for example up to 40% by weight, such as up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight up to 0.1% by weight of other compounds such as other saponins or other adjuvant materials.

The composition according to the invention may comprise a mixture of at least two iscom complexes, chosen from iscom matrix complexes, each complex comprising essentially one different saponin fraction from *Quillaja Saponaria* Molina as described in WO 2004/004762 (PCT/SE03/01180).

Preferably mixtures of matrix are used in which the fraction *Quillaja Saponaria* Molina and fraction Quil C are separately incorporated into different iscom complexes or matrix. As mentioned above any combinations of weight % of the different iscom complexes based on their content of fraction A and C of *Quillaja Saponaria* Molina respectively may be used. The mixtures may comprise from, 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60%, by weight, 50 to 50% by weight, 55 to 45% by weight, 60 to 40% by weight, 65 to 35% by weight, 70 to 30% by weight, 75 to 25% by weight, 80 to 20% by weight, 85 to 15% by weight, 90 to 10% by weight, 95 to 05% by weight, of iscom matrix complexes comprising fraction A of *Quillaja Saponaria* Molina (as herein defined) and the rest up to 100% in each case of interval of iscom matrix complexes comprising fraction C of *Quillaja Saponaria* Molina (as herein defined), counted on the content of the sum fractions A and C of *Quillaja Saponaria* Molina in the iscom matrix complexes.

The mixture may comprise from 75% to 99.5% by weight of fraction A and 0.5% to 25% by weight of fraction C. Preferably, the mixture comprises from 90% to 99% by weight of fraction A and 1% to 10% by weight of fraction C. A particularly preferred preparation comprises about 91% to 98% by weight of fraction A and about 2% to 9% by weight of fraction C, especially about 92% to 96% by weight of fraction A and about 4% to 8% by weight of complexes of fraction C counted on the content of the sum fractions A and C of *Quillaja Saponaria* Molina in the iscom complexes.

All intervals mentioned above may be used for any combination of any fraction of *Quillaja Saponaria* Molina in formulations for administration to any type of human or animal species. Examples of animal species to which the formulations according to the invention may be administrated are companion animals such as cats, dogs, horses, birds such as parrots, economical important species such as cattle, e.g. bovine species, swines, sheep, goats. Preferably more than 50% by weight of fraction C is used in combination with any of the other fractions and especially in combination with fraction A. Thus, from 50.5-99.5% by weight of C and 0.5-49.5% by weight of A may be used.

According to one embodiment of the invention the iscom matrix complex comprise fraction A of Quil A together with at least one other adjuvant as described in WO 2005/002620 (PCT/SE2004/001038). Such iscom complex and Iscom matrix complex may comprises 50-99.9% of fragment A of Quil A and 0.1-50% of fragment C and/or fraction B and/or other fractions or derivatives of Quil A counted on the total weight of fractions A and C, wherein the different glycoside components may be integrated into, coupled on to or mixed with the same or different complex or iscom matrix particles.

The truncated fibronectin binding protein and/or a fibronectin binding peptide, that comprises at least one fibronectin binding domain, may also be integrated into, coupled to or mixed with liposomes. Liposomes can be produced as described in Gregoriadis, G., McCormack, Obrenovic, M., Perrie, Y. and Saffie, R. In Vaccine Adjuvants, Preparation Methods and Research Protocols. (2000) Ed. O'Hagan D., pp 137-150. Liposomes as immunological adjuvants and vaccine carriers.

They may also be integrated into, coupled to or mixed with and/or at least one lipid and at least one saponin, whereby the at least one lipid and the at least one saponin may be in complex, solution or suspension. Preferably the complex here is not in the iscom form.

The fibronectin binding protein, the truncated fibronectin binding protein and the fibronectin binding peptide that comprises at least one fibronectin binding domain may be considered as antigens. The composition according to the invention may comprise at least one further antigen.

According to one embodiment of the invention the at least one further antigen are antigens in the form of whole cells of gram-positive bacteria.

In another embodiment of the invention the antigens are antigenic components such as from the bacterial cell or excreted products such as α and β haemolysins especially from gram-positive micro organisms.

The gram-positive bacteria from which these whole cells and antigenic components are obtained may be *Staphylococcus aureus, Streptococcus pyogenes, Streptococcus dysgalactiae Streptococcus agalactiae* and *Streptococcus uberis* and coagulase negative *Staphylococcus*, and coagulase negative *Staphylococcus*. By *Staphylococcus aureus* cells is meant the *aureus* group of the *Staphylococcus* genus. Correspondingly *Streptococcus pyogenes, Streptococcus dysgalactiae Streptococcus agalactiae* and *Streptococcus uberis* and coagulase negative *Staphylococcus*, and coagulase negative *Staphylococcus* refer to the respective group of the genus. This also applies to the micro organisms from which the FnBp binding protein, peptide or domain are obtained.

Adhesins may be chosen from clumping factor (clf), external fibrin binding protein (efb), A and B Adhesins to fibrinogen, Coagulase (coa), fibrogen binding protein A is binding to fibrinogen Fibronectin binding protein (FnBp) A and B; attachment to fibrinogen, collagen binding protein (cna); binding to collagen, Elastin binding protein (ebpS); binding to elastin, MHC analogous protein (map or eap); binding to extra cellular matrixproteins, Polysaccharide intracellular adhesin (pia); intracellular adhesion and biofilm formation, Protein A (spa); possible evasion of host defence, Capsular polyscharides (e.g. types 1, 5, 8 and 13)(cap); antiphagocytic molecules or Techoid acid.

Pore forming factors, may be excreted and may be chosen from alpha-haemolysin, beta-haemolysin, gamma-haemolysin, delta-haemolysin, Phopholipase C (plc; lysis of host cell, Elastase (sepA) tissue invasion, and Hyaluronidase (hysA) tissue invasion.

All mentioned components may be proteins or carbohydrates isolated from the bacterial cells, excreted products, rDNA products or fusion products expressed as rDNA products, products or fusion proteins in vector systems, so called DNA or RNA vaccines as long they use the present adjuvant system.

According to sill another embodiment of the invention the antigens may be antigenic components that down regulate the immune system such as super antigens, capsular antigens, endotoxins, exotoxins and extra cellular enzymes.

Such exotoxins and extra cellular enzymes may be chosen from enterotoxins A to E, H (sea-e, h), Toxin shock syndrome toxin-1 (tst); evasion of host defence with super antigen, properties, exfoliation toxins AB (eta, efb, etb, evas of host defences, Li-pase (geh); evasion of host defence, Panton-Vallentine leukociddin (lukF, lukS), lysis of host phagocytes, evasion of host defence, Staphylokinase (sak) evasion of host defence.

The antigenic components mentioned above may differ between species from the groups of the genus from different regions of the world.

The information above about the origin of the truncated fibronectin binding protein and/or a fibronectin binding peptide is also applicable to the at least further antigen that the composition may comprise.

The compositions according to the invention may further comprise a pharmaceutically acceptable carrier, diluents, excipient or additive.

The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic. The compounds of general formula I may be administered parenterally. The term parenteral as used herein includes subcutaneous injections, intravenous, intramuscular, intradermal injection of infusion techniques, for needle less injection—jet injection.

The composition may be in form of a vaccine composition for jet injector comprising some hundred doses for the vaccination of e.g. 200 cows.

The Composition according to the invention may further comprise an antigen composition affecting the udder such as coagulase negative *Staphylococci, Streptococcus uberis, Streptococcus dysgalacti, Streptococcus agalacti, Coliforma* bacteria including *Klebsiella* sp.p, and *E. coli.*

The invention also relates to the use of the compositions for preparing vaccines. The vaccines are intended for any mammal such human beings, animals such as cattle, sheep or goat. The invention especially relates to the vaccination of bovine, ovine and caprine animals against mastit. The invention especially relates to a mastit vaccine for bovines comprising an antigen from against *Staphylococcus aureus* mixed with iscom matrix. The matrix is preferably produced from crude Quil A or semi purified Quil A.

The bovines may be vaccinated once before calving and a booster before or after calving, (preferably after) 1 month. Heifers may be given to two administrations before calving, preferably possibly followed by a third administration after calving.

One embodiment of the invention relates to a composition according to claim 1 comprising at least one further antigen chosen from toxins and/or whole cells from a micro organisms especially from gram-positive bacteria such as *Staphylococcus aureus, Streptococcus pyogenes, Streptococcus dysgalactiae Streptococcus agalactiae* and *Streptococcus uberis* and coagulase negative *Staphylococcus*, especially form *Staphylococcus aureus*. Thus the composition may comprise toxins or whole cells or both.

It has turned out that for heifers above about one year of age better immunisation is obtained when a composition according to the invention is used supplemented with whole cells and/or toxins from gram-positive bacteria, especially from the ones mentioned above such as *Staphylococcus aureus.*

The invention further relates to kit of parts wherein one compartment comprises at least one fibronectin binding protein and/or at least one truncated fibronectin binding protein and/or at least one fibronectin binding peptide, that comprises at least one fibronectin binding domain, and another compartment comprises an instruction for use and/or at least one iscom matrix complex and/or a liposome.

Gram-positive micro organism species mentioned above, such as *Staphylococcus aureus* species from the *aureus* group of the *Staphylococcus* genus, may differ from different regions of the world. One compartment of the kit may comprise an iscom matrix complex or liposome according to the invention. This compartment may comprise one or more antigens from a gram-positive micro organism e.g. the *aureus* group of the *Staphylococcus* genus. The other compartment may comprise an antigen from a gram-positive micro organism, e.g. form the *aureus* group of the *Staphylococcus* genus that may be specific for a certain region e.g. based on capsular antigens. Both types of antigen may be integrated into liposomes, bound to liposomes or iscom matrix complex or mixed with iscom matrix complex or liposomes.

As the gram-positive micro organism species mentioned above, such as *Staphylococcus aureus* species from the *aureus* group of the *Staphylococcus* genus, may elicit antigens that down regulate the immune system and antigens that does not down regulate the immune system it could be advantageous to administrate these different types of antigens in different formulations to different parts of the animal body to increase the effect of each components following the immunisation. Kits may therefore comprise at least one compartment comprising at least one antigen that down regulate the immune system and another compartment comprising at least one antigen does not down regulate the immune system.

The composition and the kit may also comprise an antibiotic. This may be useful when the animal has a sub clinical or clinical infection of the above mentioned micro-organisms.

The amount of antigenic substance might vary, dependent on the substance and micro-organisms used and the individual to be treated. For small animals the low dose is 0.1 μg up to 100 μg, for large animals the low dose range from 10 μg up to 1000 μg, especially 10 μg up to 300 μg that said not to be limiting borders. In humans the dose ranges are 1 μg up to 200 μg not being the limiting border.

The invention also relates to a method for vaccination of mammals such as human beings and especially cattles, wherein a composition comprising at least one fibronectin binding protein, and/or at least one a truncated fibronectin binding protein and/or at least one fibronectin binding peptide, that comprises at least one fibronectin binding domain, and at least one iscom matrix complex and/or liposome is administrated to the animal.

Immunization protocol for a prospective mastitis vaccine may be as follows:

For heifers going into lactation two immunizations are carried out s.c. with 5 to 8 weeks interval. The last immunization is done round ten days before calving. After that it is recommended with a yearly immunization 10 to 14 days before expected calving.

In the case a cow that has a sub clinical or a clinical SA mastitis it will be recommended to vaccinate twice with 2 to 3 weeks interval during the dry period and in that connection treat the cow with antibiotic i.e. a combined immunological and antibiotic treatment.

All information regarding the fibronectin binding protein, the truncated fibronectin binding protein and/or a fibronectin binding peptide, that comprises at least one fibronectin binding domain, the lipids, glycosides and other added antigens besides the fibronectin binding protein or peptide relate mutatis mutandis to all embodiments of the invention.

While the invention has been described in relation to certain disclosed embodiments, the skilled person may foresee other embodiments, variations, or combinations which are not specifically mentioned but are nonetheless within the scope of the appended claims.

All references cited herein are hereby incorporated by reference in their entirety.

The expression "comprising" as used herein should be understood to include, but not be limited to, the stated items.

The invention will now be further elucidated by way of the following non limiting examples.

EXAMPLES

General Information for Examples

Materials

Adjuvants

Al(OH)3—A classical adjuvant for use in animals and in humans. The adjuvant effect is still not fully understood. Antibody responses are enhanced compared with no adjuvant but the response is strongly TH2 biased. No or low adjuvant effect on cellular responses.

Al(OH)3, Allhydrogel was from Brenntag AG, Denmark.

Iscom Matrix Adjuvants

Matrix-Q—is produced from semi-purified Quillaja saponin containing a whole range of different Quillaja saponin molecules. The adjuvant effect is strong and includes both humoral and cellular immune responses.

Matrix-C is produced from one purified fraction of Quillaja saponin (Fraction-C). It has a potent adjuvant activity (Johansson, M and Lövgren-Bengtsson, K Vaccine 17, 2894-2900). Toxicity is considerably lower than that of Matrix-Q.

Matrix-QWT is produced from another purified fraction of Quillaja saponin (Fraction-A). The adjuvant effect is described as lower that for Matrix-C (PCT/SE2004/001038) but it appears to be strong for cellular immune responses.

Matrix-QWT appears to be essentially non-toxic in doses relevant for adjuvant activity and is very well tolerated in all animal species tested.

Matrix-MIX—is a mixture of Matrix-QWT and Matrix-C (consisting of 17% Matrix-C and 83% Matrix-QWT). Similar mixtures were shown to exert surprisingly high adjuvant effect for single antigens (WO 2004/004762, PCT/SE2004/001038). All matrixadjuvant formulations were from Isconova AB, Uppsala, Sweden.

Antigens

Formalin treated Tetanus toxoid (TT) was from The State Serum Institute, Copenhagen, Denmark. TT is a considerably immunogenic antigen. A higher dose (2.5 lf) and a low dose (0.5 Lf) were used in the examples. For this particular batch, 1 Lf of toxoid corresponds to x micrograms of protein.

Recombinant Diptheria toxoid (DT) was from Sigma. A dose of 1 microgram was used in the examples.

Fibronectin binding protein (FnBp) was manufactured by Crosslink Ltd Budapest Hungary and was a mixture of FnBp A Short (396 bp with 100% conformity of FnBp A of NC__002951.2) and FnBp B Short (396 bp with 95% conformity of FnBp B of NC__002951.2 and from Biostapro AB Ulltunaallen 2B 756 51 Uppsala, Sweden and was a DNA fragment including a 16 kD fibronectin binding domain including 3 DD repeats including a cystein N terminal not essential for the immunization result. 190 µg of this construct was mixed with 1 mg iscom matrix per dose.

ELISA

Mouse sera. Antigen specific antibodies in serum were measured in individual samples by conventional indirect ELISA. Microtiter plates (Nunc, Roskilde, Denmark) were coated over night at +4° C. with the individual antigens at a concentration of 1 µg/ml in 50 mM carbonate buffer pH 9.6. Prior to incubation with samples, the plates were blocked for 1 hour at r.t. with PBS-T (Phosphate Buffered Saline with 0.05% Tween) supplemented with 2% (w/v) fat free milk powder (PBS-T/M). The plates were incubated sequentially with serial dilutions of test sera in PBS-T/M and HRP-conjugated rabbit anti-mouse IgG (Dakocytomation, Denmark). For measurement of IgG subclasses, serial dilutions of test sera were incubated with HRP-conjugated goat-anti-mouse IgG1HRP (Serotec, Norway) or with HRP-conjugated goat-anti-mouse IgG2a HRP (Serotec, Norway). The enzyme reaction was visualised by incubation with substrate buffer (K-blue, SVANOVA, Uppsala, Sweden), the reaction was stopped after 10 minutes by addition of 50 µl 2 M H2SO4 and the absorbance was read at 450 nm. All washings were done with PBS-T. Conjugates were diluted according to the manufacturers instructions in PBS-T/M. Titres were calculated by interpolation of the linear part of the titration curve and are expressed as reciprocals of the serum dilution giving an absorbance of 1.0.

Cow sera and milk. Antigen specific antibodies in serum and milk were measured in individual serum (milk) samples by conventional indirect ELISA. Microtiter plates (Nunc, Roskilde, Denmark) were coated over night at +4° C. with FnBp at a concentration of 1 µg/ml in 50 mM carbonate buffer pH 9.6. Prior to incubation with samples, the plates were blocked for 2 hour at r.t. with PBS-T (Phosphate Buffered Saline with 0.05% Tween) supplemented with 10% (w/v) horse serum (PBS-T/H). The plates were incubated sequentially with serial dilutions of test sera (milk) in PBS-T/H and HRP-conjugated sheep anti-bovine IgG (Serotec, Norway). For measurement of IgG subclasses, serial dilutions of test sera were incubated with HRP-conjugated sheep anti-bovine IgG1 (Serotec, Norway) or with HRP-conjugated sheep anti-bovine IgG2 HRP (Serotec, Norway), with HRP-conjugated sheep anti-bovine IgA
(Serotec, Norway) The enzyme reaction was visualised by incubation with substrate buffer (K-blue, SVANOVA, Uppsala, Sweden), the reaction was stopped after 10 minutes by addition of 50 µl 2 M H2SO4 and the absorbance was read at 450 nm. All washings were done with PBS-T. Conjugates were diluted according to the manufacturers instructions in PBS-T/H. Titres were calculated by interpolation of the linear part of the titration curve and are expressed as reciprocals of the serum dilution giving an absorbance of 1.0.

Antibodies against Staphylococcal bacteria were measured in serum and milk using a commercial ELISA (*Staphylococcus Aureus* Antibody Test Kit, WMRD, Pullman, Wash., USA).

Example 1

Preparation of Fibronectin Binding Domains

| Cloning of Fibronectin Binding Protein | | |
|---|---|---|
| Project carried out by Crosslink Ltd. Budapest, Hungary | Report written by Ferenc Felföldi, Crosslink Ltd. | Ordered by Prof. Bror Morein ISCONOVA, Uppsala, Sweden |

Content Introduction p 1
A. Cloning of the full length version with 6-His tag at C terminal p 1
B. Cloning of the short version with 6-His tail at the C terminal p 3

Introduction

The aim of the project was to clone and express FNBP gene from *Staphylococcus aureus*
  a.) full length version with 6-His tag at C terminal for protein preparation;
  b.) short version with 6-His tail at the C terminal for linking to the adjuvant;

The strain which cause mastitis in cows was provided by the ISCONOVA Ltd., Uppsala, Sweden. However, sequence information of this strain was not available.

A. Cloning of the Full Length Version with 6-His Tag at C Terminal

In *S. aureus* two types of gene code for Fibronectin Binding Protein, i.e., FNBP A and FNBP B gen. We investigated the NCBI Data Bank (www.ncbi.nlm.nih.gov/blast) for FNBP and found sequences for eight *S. aureus* strains.

There was only 80% similarity of the eight strains in the FNBP genes. In order to be sure that the FNBP gene of our strains can be amplified on the full length (excluding the signal sequence), we had to select primers which amplify both A and B genes.

Preparation of Target DNA from *Staphylococcus aureus*.

The genomic DNA was prepared from *S. aureus* suspension by traditional method and used in PCR reaction as template. Fortunately the length of the A and B gene is differs by 200 bp. Thus, in a long electrophoresis gel the separation of the two PCR products was possible. The A gene product was separated and used in the following steps.

1. Fifty ml *S. aureus* culture (OD600=2) were centrifuged and washed two times in 2×25 ml washing buffer (150 mM NaCl, 50 mM Tris HCl [pH: 7.5]).
2. The cells were resuspended in 5 ml lysis bufferA (10 mM EDTA, 50 mM Tris HCl [pH: 7.5], 0.1 mg/ml lyzozym) and kept on room temperature for 15 min.
3. Five ml lysis bufferB (2% SDS, 50 mM Tris HCl [pH: 7.4], 0.025 mg/ml Proteinase K) was added. The suspension was incubated at 55° C. for over night.
4. The suspension was extracted with one volume phenol followed with extraction with one volume chloroform+i-amylalcohol.
5. The DNA was precipitated with 2.5 volume ethanol and spined onto a glass rod. The DNA was washed with 70% ethanol and dried in Eppendorf tube.
6. The DNA was resuspended in 250 microliter TE buffer.

In the next step we digested both PCR products with different restriction enzymes in order to select those, which don't have cleavage site in the PCR products. They can ensure cloning at the ends without damaging the insert.

We found three restriction enzymes, BamHI, HindIII and XhoI that do not cleave into FNBP A. We decided to go on with FNBPA, and the BamHI and HindIII to be used for cloning, while the XhoI for His tag addition to the C terminal.

The primers used for amplifications have the above cleavage sites at their 5' end (bold text):

```
FnBpaF
CGGGATCCTGCAGCATCAGAACAAAAGACAACTACAGT
(SEQ ID NO: 1)

FNBPaR
GTAAGCTTATGCTTTGTGATTCTTTTTATTTCTGCGTAA
(SEQ ID NO: 2).
```

Amplification of the FNBP Gene:

The full length of FNBP A gene from the desired strain was amplified, cloned and confirmed by sequencing.

In order to make later purification more efficient, the membrane binding domain (M) and the repetitive and non repetitive part of cell-wall spanning domain (W1 and W2) of the gene was removed.

For the domain descriptions see article Signas et al.: (1989 loc.cit.)

NcoI and the above mentioned XhoI restriction enzymes were proper for this aim.

The designed primers where:

```
FnBpNco
CGGGATCCATGGCATCAGAACAAAAGACAACTACAGT (SEQ ID NO: 3)
(primer starts at pos. 2572388 OF
>ref|NC 002951.2| Staphylococcus aureus subsp.
aureus COL, complete genome Length = 2809422)

FnBpD4
GAGCTCGAGTGGCACGATTGGAGGTGTTGTATCTTCT (SEQ ID NO: 4)
(primer starts at pos. 2569863 OF
>ref|NC 002951.2| Staphylococcus aureus subsp.
aureus COL, complete genome Length = 2809422).
```

The following steps were used
1. One hundred microliter amplification solution contained 10 microliter 10×PCR buffer, 10 microliter of each primer (10 pmol/microliter stock), 400 micromol dNTP and 5 U Pfu enzyme.
2. The amplification was carried out in 30 cycles of denaturation (94° C. for 45 s), annealing (65° C. for 1 min) and polymerisation (72° C. for 2 min.).
3. The PCR products were checked in agarose gel and purified by Single Sample PCR Cleanup Montage® PCR Filter Units (Millipore).

Cloning of the PCR Product

The FNBP gene was cloned into pET21d vectors. A codon for 6-His tag, followed by a stop codon, is situated behind the XhoI cleavage site of the pET21d vector. As a consequence, the expressed protein will contain a 6-His tag at the C terminal.

The expression was carried out for 8 hours after induction. The cells were sonicated and centrifuged after expression. The products were tested on SDS-PAGE and commassie blue staining with or without preparation on Ni-NTA agarose column. The expression was clear compared to the non-induced culture.

The following steps were used
1. The PCR product was resuspended in 40 microliter NEB2 buffer and digested at 37° C. for 2 hours by NcoI and XhoI restriction enzymes.
2. The digested fragment was purified from gel by Montage Gel Extraction Kit (Millipore).
3. The purified DNA was cloned into the pET21d vectors at the NcoI/XhoI site in 50 microliter reaction solution. The vector and the insert were ligated over night by 11 U ligase enzyme.
4. The plasmid was precipitated with 2.5 vol. ethanol, resuspended, and used for electroporation (Bio-Rad) into *E. coli* BL21 strain according to the instruction of the supplyer.
5. The clones were cultured in LB media and the insertion of the FNBPA gene into the vector was checked by NcoI/XhoI digestion, followed by gel electrophoresis.
6. The appropriate vector was transformed into the *E. coli* BL21 strain again, grown in 20 times 30 ml parallel culture in LB media. The cells were induced with 1 mM IPTG at OD600=1.

B. Cloning of the Short Version with 6-His Tail at the C Terminal

The short version was cloned with the following primers. The cleavage sites of the NcoI restriction enzyme and the XhoI restriction enzyme indicated by bold letters.

```
BGF
CGGGATCCATGGAAGGTGGCCAAAATAGCGGTAACCAGT
(primer starts at pos. 2570270 OF
>ref|NC 002951.2| Staphylococcus aureus subsp.
aureus COL, complete genome Length = 2809422)

BGR
GAGCTCGAGAGGTGTTGTATCTTCTTCAATCGTTTGTTG
(primer starts at pos. 2569875 OF
>ref|NC 002951.2| Staphylococcus aureus subsp.
aureus COL, complete genome Length = 2809422)
```

The PCR product made with these primers were cloned into the pET21d vector and expressed in BL21 (DE3) Star cells. A codon for 6-His tag, followed by a stop codon, is situated behind the XhoI cleavage site of the pET21d vector. As a consequence, the expressed protein will contain a 6-His tag at the C terminal.

The expression was carried out for 8 hours after induction and the expressed product was purified on Ni-NTA column and visualised in SDS-PAGE gel. The expression was clear compared to the non-induced culture.

Larger amount of the protein was prepared as follows.
FNBP Production with FNBP(AB)BL21 (DE3) Star Strain
Culture:
Medium: Four litre LB+2 g/L glucose+100 ug/mL Amp,
at 37° C. up to OD 1.5, reduce temp to 30° C., induction with
1 mM IPTG
at OD 2-2.5 for 5 hours
Downstream:
Pellet the culture by centrifugation
Resuspend in buffer: 10 mM Tris, pH8, 150 mM NaCl
Pellet by centrifugation, resuspend in 40 ml 25 mM Tris pH8
Sonicate 10×30 s with 1 min pause between.
Add PMFS for 5 mM final concentration.
Pellet with 20000 g. for 25 min. Supernatant to be saved.
Resuspend pellet in 40 ml 25 mM Tris pH8.
Sonicate as above.
Add PMFS for 5 mM final concentration.
Mix supernatant with previous supernatant. Total volume approx. 90 ml.
Apply supernatant on 10 ml Ni-NTA agarose column (with binding capacity 5-10 mg protein/ml gel) equilibrated with sonication buffer (25 mM Tris pH8).
Wash with 1 volume sonication buffer.
Wash with 2 volume 25 mM Tris HCl pH: 6.8, 250 ml NaCl
Wash with 1 volume 25 mM Tris HCl pH: 8, 8 M Urea
Wash with 2 volume sonication buffer.
Elute with 200 mM imidazol pH7.
Add TCA to 10% final concentration, put for 1 hour to 4° C.
Pellet the protein.
Add 0.2 ml 1M Tris HCl pH8 and fill up to 1 ml with TE buffer.
Dissolve protein in sonicator with water bath.
(Option: for delivery protein can precipitate with ammonium sulphate.)

A corresponding FnBp A protein was constructed with the same strategy and delivered by Crosslink Ltd. Budapest, Hungary as follows:

Three tubes containing 2 mg proteins (each). The proteins were purified on Ni-NTA column. The final step was the precipitation with ammonium-sulphate and centrifugation to create the pellet.

What to do: Take up in a weak buffer. Preferably use sonicator with a water bath which promotes dissolving without foam building. Remove the salts on PD-10 column (Amersham).

One tube containing 3.1 mg protein. Same as the other three, but without centrifugation.

What to do: Put the tube at 4° C. for one hour. Centrifuge by 15.000 g or more for 20 minutes. Remove the supernatant. Use the same procedure as above.

The protein is a mixture of FnBpA (SEQ ID NO:7) and FnBpB (SEQ ID NO:8) gene with His tag at the end. The Mw is 16 kDa.

The product was used in the experiments performed in Examples 6 and 7

A corresponding FnBpA protein was produced by Biostapros AB according to the same strategy. Two constructs were made with Cys at the N and C terminal respectively. A 50% mixture of each was used in Examples 2-5.

```
FNBP Cys-N
MACEGGQNSGNQSFEEDTEEDKPKYEQGGNIVDIDFDSVPQIHGQNKGNQ
SFEEDTEKDKPKYEHGGNIIDIDFDSVPHIHGFNKHTEIIEEDTNKDKPS
YQFGGHNSVDFEEDTLPKVSGQNEGQQTIEEDTTPG (SEQ ID NO: 9)

FNBP Cys-c
MEGGQNSGNQSFEEDTEEDKPKYEQGGNIVDIDFDSVPQIHGQNKGNQSF
EEDTEKDKPKYEHGGNIIDIDFDSVPHIHGFNKHITEIIEEDTNKDKPSY
QFGGHNSVDFEEDTLPKVSGQNEGQQTIEEDTTPCG (SEQ ID NO:
  10)
```

Example 2

Introduction

*Staphylococcus aureus* (SA) is a pathogen for most mammalian species causing acute and chronic infections in wounds including those caused by surgical treatments, in the mammary glands or in man also nosocomial infections. SA is often resistant to antibiotic and the alternative would be a vaccine at least for prophylactic use but, so far, there is no efficient vaccine although many attempts to formulate vaccines have been made including whole cells, toxins, polysaccharides and adhesion factors. To succeed with a vaccine formulation against a pathogen with the propensity for causing chronic infections the aid of an adjuvant system is essential when non-replicating antigens are used. Thus, the failure of the various components of SA that are of interest and tested as vaccine antigens including adhesion factors, carbohydrates (polysaccharides) and toxins might be due to the lack of an appropriate adjuvant that is acceptable for the species involved. In this example we have chosen an adhesion factor i.e. fibronectin binding protein (FnBp), which is considered to block adhesion but probably more importantly to be target for phgocytosis if right antibodies (opsonizing antibodies) are evoked to FnBp promoting this activity. Furthermore, the FnBp has been complemented with various adjuvant formulations based on the iscom technology including those that are acceptable for sensitive species.

Thus, different animals species require different adjuvant formulations including different saponins. The bovine species e.g. responds very well to a semi-purified saponin of QuilA or Q-WAC types, which might be toxic for other species. Other animal species e.g. cat or mice or man are sensitive to various degree and require a virtually non-toxic formulation as e.g. QMIX (QV-MIX Swedish patent application:

```
FnBpA   1 MEGGQNSGNQSFEEDTEEDKPKYEQGGNIVDIDFDSVPQIHGQNKGNQSF 50
          |||||||||||||||||||||||||||||||||||||||||||| |||||
FnBpb   1 MEGGQNSGNQSFEEDTEEDKPKYEQGGNIVDIDFDSVPQIHGQNNGNQSF 50

51 EEDTEKDKPKYEHGGNIIDIDFDSVPHIHGFNKHTEIIEEDTNKDKPSYQ 100
          ||||||||||||| |||||||||||||||||||||||||||||||| ||
       51 EEDTEKDKPKYEQGGNIIDIDFDSVPHIHGFNKHTEIIEEDTNKDKPNYQ 100

101 FGGHNSVDFEEDTLPKVSGQNEGQQTIEEDTTPLEHHHHHH* 142
          |||||||||||||| ||| ||||||||||||||||||||||
      101 FGGHNSVDFEEDTLPQVSGHNEGQQTIEEDTTPLEHHHHHH* 142
```

0202110-3—QV-MIX PCT/SE 03/001180) or QWT formulations (QWT Swedish patent application: 0301998-1 PCT/SE 03/00586), or a fraction C-matrix formulation (ref). The latter is used in veterinary medicine and in clinical trails for man. The goal is a balanced immune response promoting neutralizing as well as antibody class promoting phagocytosis i.e. in the murine species IgG2a, while IgG1 is likely to promote anti-adhesion and neutralization effects. In this example these immunological properties are analysed.

It should be noted that SA is an important pathogen for most if not all mammalian species and that the results from a mastitis vaccine has bearing on SA caused diseases in other species including man.

The composition of vaccine antigens might vary in vaccines against SA infections and SA caused disease depending on several factors including local strains, clinical pictures. The adhesion to fibronectin mediates an important factor for the infection process, and this protein is present on virtually all SA isolates. The blocking of adhesion and neutralization is an effect by IgG1 by antibodies, while IgG2a is important for phagocytosis the major immune protective mechanism against SA. The subclasses mentioned reflect the murine immunoglobulin system, while e.g. IgG2a corresponds to IgG3 in the human. The immune response in mice to the strong vaccine candidate FnBp adjuvanted with the QWT-matrix formulation is analysed with regard to the balance between the IgG immunoglobulin classes reflecting T-helper 1 and 2 responses.

Experimental Lay Out 18 g female Balb/c mice were immunised as indicated in Table 1:1. The antigen dose was determined from earlier experiments to be immunogenic. A low dose was selected, not inducing high responses, in order to see the influence of the added adjuvant. The mice were immunized with either of the FnBp adjuvans formulations 4 weeks apart subcutaneously (s.c.) at the root of the tail. Blood samples for serum testing were taken at weeks 3 and 6. All animals received 1 µg of FnBp and the adjuvant component was in; gr.1 non-adjuvanted, gr.2 Al(OH)3; gr.3 Matrix-Q 6 µg; gr. 4 Matrix-Q 2 µg. The antigen specific antibody responses in IgG1 and IgG2 subclasses at week 6 are shown in FIG. 1:1. The antibody levels were measured in ELISA and expressed as the dilution (10 log) at the OD 450 being the steep part of the dilution curve reading on the Y-axis (FIG. 1:1).

Results

After the first immunization the non-adjuvanted and the aluminiumhydroxide-adjuvanted FnBp did hardly induce detectable serum antibody response. The various formulations of FnBp adjuvanted with any of the iscom adjuvanted formulations induced detectable responses to FnBp.

After the second immunization (FIG. 1:1) the IgG1 response was high (>10 log 4) in mice groups of mice immunized with FnBp adjuvanted with iscom matrix. In groups of mice given Matrix-Q high or matrixMIX and there was little spread of titres among individual mice while high in the group where the mice were given FnBp in the matrixC formulation. The mice immunized with aluminium hydroxide adjuvanted FnBp responded with significantly lower IgG1 serum antibody levels than other adjuvanted FnBp formulations and with large spread of ELISA titres among the individual animals. Mice immunized with the non-adjuvanted formulation responded with a low IgG1 response.

After the second immunization (FIG. 1:1) the IgG2a response was high (>10 log 4) in mice groups of mice immunized with FnBp adjuvanted with iscom matrix. In groups of mice given Matrix-Q high or matrixMIX and there was little spread of titres among individual mice while the spread was high in the group where the mice were given FnBp in the matrixC formulation. The mice immunized with non-adjuvanted FnBp or with aluminium hydroxide adjuvanted FnBp responded with hardly detectable IgG2a serum antibody levels.

Discussion

It is clearly shown that the iscom formulations have capacity to modulate a balanced immune response including both TH1 and TH2 types of immune responses, which is essential to induce protection against persistent and chronic infections. So far the adjuvant formulations used in SA vaccines have lacked this capacity Conclusion Two interesting formulations for SA and FnBp are the matrixQ suitable for the large animals like the bovines and the Low-Tox matrixC & matrixA in different particles virtually free of side effects and e.g. suitable for cats and human beings. Both these formulations induced high and balanced IgG1 and IgG2 responses.

Example 3

Introduction

A vaccine against SA may include or even require various vaccines components including whole cells, toxins, polysaccharides and adhesion factors, each one contributing to immune protection. In the present example tetanus toxiod (TT) is tested with the different adjuvant formulations as in example 2 to explore their immune enhancing effect on a toxin.

Experimental Lay Out 18 g female Balb/c mice were immunised as indicated in Table 2:1. The antigen dose was determined from earlier experiments to be immunogenic but not inducing very high responses in order to see the influence of the added adjuvant. The mice were immunized with either of the TT adjuvans formulations 4 weeks apart subcutaneously (s.c.) at the root of the tail. Blood samples for serum testing were taken at weeks 3 and 6. All animals received 0.5 Lf/dose and the adjuvant component was in; gr.1 non-adjuvanted, gr. 2 Al(OH)3; gr.3 Matrix-Q 6 µg; gr. 4 Matrix-Q 2 µg. The antigen specific antibody responses in IgG1 and IgG2 subclasses at week 6 are shown in FIG. 2:1. The antibody levels were measured in ELISA and expressed as the dilution (10 log) at the OD 450 being the steep part of the dilution curve reading on the Y-axis (FIG. 2:1).

Results

After the first immunization the non-adjuvanted and the aluminiumhydroxide-adjuvanted TT did induce detectable serum antibody response like the various formulations of TT adjuvanted with any of the iscom formulations.

After the second immunization (FIG. 2:1) the IgG1 response was high (>10 log 4) in all mice groups including non-adjuvanted TT. Slightly higher antibody levels against TT were observed in groups of mice given TT adjuvanted with the iscom matrix formulations and there was little spread of titres among individual mice.

After the second immunization (FIG. 2:1) the IgG2a response was high (>10 log 5) in mice groups of mice immunized with TT adjuvanted with iscom matrix. Mice in the groups given TT adjuvanted with matrix-Q or with matrix MIX responded with highest IgG2a levels and there were little spread of titres among the individual mice. The mice immunized with non-adjuvanted TT or with aluminium hydroxide adjuvanted TT responded with no or hardly detectable IgG2a serum antibody levels.

Discussion

TT has a strong antigenic capacity towards a Th2 type of response. Aluminium hydroxide is also modulating towards the Th2 type of immune response. This example shows that the iscom formulations overcome the strong immune modulatory effect of TT and can induce a balanced Th1-Th2 response to this toxin. It is important for a vaccine against a pathogen inducing chronic or persistent infection to override the intrinsic capacity of this pathogen to modulate the immune response in the host, which the weak adjuvant not can do.

Conclusion

This example shows that the iscom formulations have capacity to modulate immune response of "strong toxin antigens" to a balanced immune response, which can be required to achieve immune protection. Toxins are important pathogenicity factors for SA as well as for other pathogens and might therefore be required to obtain a potent vaccine.

Example 4

SA is producing a number of toxins some of which are strongly immunogenic other are comparatively weakly immunogenic. Any of those may be required vaccine antigens to obtain a vaccine that has very broad protective capacity. Diptheria Toxoid (DT) is a relatively weak antigen in contrast to TT. In this example a weak antigen is tested with the different adjuvant formulations as in example 2 and 3 to explore their immune enhancing effect on a DT type of toxin.

Experimental Lay Out 18 g female Balb/c mice were immunised as indicated in Table 3:1. The antigen dose was determined from earlier experiments to be immunogenic but not inducing very high responses in order to see the influence of the added adjuvant. The mice were immunized with either of the DT adjuvans formulations 4 weeks apart subcutaneously (s.c.) at the root of the tail. Blood samples for serum testing were taken at weeks 3 and 6. All animals received 1 µg of DT and the adjuvant component was in; gr.1 non-adjuvanted, gr.2 Al(OH)3; gr.3 Matrix-Q 6 µg; gr. 4 Matrix-Q 2 µg. The antigen specific antibody responses in IgG1 and IgG2 subclasses at week 6 are shown in FIG. 3:1. The antibody levels were measured in ELISA and expressed as the dilution (10 log) at the OD 450 being the steep part of the dilution curve reading on the Y-axis (FIG. 3:1).

Results

After the first immunization only mice immunized with the DT adjuvanted with the Matrix-MIX formulation responded with detectable serum antibody response.

After the second immunization (FIG. 3:1) the IgG1 response was highest (>10 log 3.5) in mice immunized with aluminiumhydoxide- and matrix mixed adjuvanted DT.

After the second immunization (FIG. 3:1) the IgG2a response was high (about 10 log 4) in mice in the group immunized with DT adjuvanted with adjuvanted with matrix MIX responded with the highest antibody levels i.e. almost 50 fold higher titres or more than mice in other groups and the spread of titres was lower. The mice immunized with non-adjuvanted DT or with aluminium hydroxide adjuvanted DT responded with no or hardly detectable IgG2a serum antibody levels.

Discussion

DT is a weaker antigen than TT (example 3) and no-adjuvantes DT did not even after two immunizations induce detectable IgG1 or IgG2, i.e. neither a Th2 type of response nor a Th1 type. Aluminium hydroxide modulating towards the Th2 type of immune response enhanced the response of DT to readily detectable levels of IgG1. This example shows that the iscom formulations enhance and also modulate the immune response to DT to a balanced response between Th1 and 2. Particularly the "low-tox" matrix-MIX was efficient for stimulation of both IgG1 and IgG2 i.e. a potent and balanced immune response. Thus, iscom formulations can efficiently modulate immune responses for both strong and weak antigens.

Conclusion

The examples 2 and 3 show that the iscom formulations efficiently enhance and modulate the immune responses of toxins regardless those are weak or strong antigens and drive e.g. a Th2 biased toxin antigen towards a balanced Th1-Th2 response. Such capacity is important in a complex system of antigens that a SA antigen formulation might constitute.

Example 5

Small Scale Field Trial Immunisation Experiment with *Staphylococcus Aureus* Adhesion Factor FnBp Adjuvanted with Iscomatrix The vaccination experiment at Kungsängen (KÄ), a farm belonging to the Agriculture University Uppsala, was carried out to test a potential vaccine against *Staphylococcus aureus* (SA) in a natural host i.e. the bovine species. Mastitis is a serious problem in diary cattle and also in the related species sheep and goats when those are used for milk production. The mastitis problem is well recognised by anyone experienced in diary science and production including the producer at the diary farm, the veterinarian responsible for the animal health and the factory producing different milk products requiring high quality milk.

To control the situation of mastitis a farm-improved husbandry is the first alternative supplemented with treatment mainly by use of antibiotics. SA is the most important pathogen for the udder causing suffering and economical problems. Particularly problematic is that SA often is antibiotic resistant, and affected animals have to be culled because there is no treatment. The alternative for treatment of mastitis with antibiotics is immune prophylactics i.e. the use of vaccine. In spite of many attempts no efficient mastitis vaccine is on the market. The attempts to develop a mastitis SA vaccine have been in vain and that has also been the case with attempts to develop SA vaccines for other species in other situations e.g. against furunculosis in dogs or against nosocomial infections in human beings. Thus, an efficient vaccine against SA mastitis would rescue affected animals from suffering and have economically extremely good effects for the diary farms, for the diary industry and for their customers.

An adhesion factor, fibronectin binding protein (FnBp), was chosen because it is present in close to 100% of SA isolates. In early experiments (Nelson et al. 1991) the FnBp was incorporated into iscoms. Promising results were obtained with this SA mastitis experimental vaccine. Conversely, continued experiments did not give the desired outcome and the project was discontinued. Reasons for the failure were a short-lived immunity and probably also insufficient immune responses in the mammary gland.

The aim of this vaccination experiment was to explore the possibilities to further develop the FnBp vaccine adjuvanted with a formulation based on the iscom technology. A focus was on an optimal mode of administration to evoke immune responses both systemically, measured in blood serum and locally in the mammary gland. Thus, to obtain a better forecast for the potential of the vaccine candidate immunological analyses were also carried out on the local secretion (milk whey) from the udder. The evaluation of the immune responses included the antibody responses in serum and milk whey including IgG1, IgG2 and IgA and also looks into the enhancement by antibodies of the phagocytosis of SA cells. IgG2 is promoting phagocytosis, which is the most important defence mechanism against SA. The locally produced IgA antibodies are also important defence factor against invaders in mucosal surfaces. It should be noted that the previous experiments have not analysed the immune responses in the mammary gland most likely because previous vaccine did not induce clearly detectable immune responses in the milk whey that convincingly would support the trial. It has been conceived that the dilution of high volumes of milk would hide the immune response evoked in the mammary gland.

The Lay Out of the Vaccine Trial and Materials and Methods

The fibronectin binding protein (FnBp) of 16 kD fragment of larger a protein to include the DD region responsible for adhesion to fibronectin. The polypeptide was expressed in $E. coli$ and obtained from Biostapro AB. It differed from the previous product (Nelson et al. 1991) that was based on shorter 69 to 80 kD protein. Furthermore, in the previous product the FnBp was incorporated into the iscom matrix to form an iscom. In the present experimental vaccine the preparation of the vaccine did not encompass a step to include the FnBp in a matrix to form an iscom. Avoiding the incorporation gives the advantage of a simpler and more economical production system. Thus, the present formulation differs from two aspects from the previous tested FnBp iscom vaccine candidate.

The iscom matrix was supplied by Isconova AB.

The bacteriological examinations of milk samples were done at the mastitis laboratory at the National Veterinary Institute (SVA).

Experimental Performance

The antigen FnBp a rDNA product produced in $E. coli$ was selected because of previous positive experience (Nelson et al-), but the construct was shorter. The immunological evaluation is optimally facilitated with a defined antigen.

Ten heifers going into their first lactation were used as experimental animals to avoid as far as possible previous experience with SA infections, more likely in older cows, which would cause difficulties for the immunological evaluation of the vaccination.

Three different modes of administration were tested. Since the udder is an organ with a large mucosal area it was considered that mucosal immunity in the mammary gland is important. In contrast to, e.g. man and swine, there is no gut mammary link in the bovines (personal communication Holmberg), i.e. oral administration of vaccine antigens (i.e. in the digestive tract) will evoke immune response in the mammary gland in swine but not in cows. In this experiment two mucosal modes of administrations were employed, i.e. the primary dose was given by the intranasal (i.n.) or by the intra vaginal (i.vag.) routes. The effect of these modes of priming was compared with the priming by a s.c. immunisation in the supra mammary region. The second dose was administered to all animals by the s.c. route three to four weeks later. With this immunisation regimen it was intended to explore if a link between the upper respiratory region or the genital tract and the mammary gland exist. Important for immune protection is the mucosal (local) immune response and that right type of antibody class is evoked in the mammary gland Immunisation protocol included a primary immunisation two to four weeks before calving. Three animals were primed by i.n. administration, three animals by i.vag. mode of administration and four animals were immunised by the s.c. route in the supra mama region. The second immunisation was done for all animals after calving by the s.c. mode in the supra mammal region where lymph nodes draining the mammary gland are located.

Sampling. Blood for serum and immunological analyses were collected at the time of first immunisation and then regularly starting as indicated in the FIGS. (4:1 to 4:2). Collection of milk for bacteriological and immunological analyses of the whey started after partus and then as described for blood.

Bacteriological analyses were carried out at SVA and only at one occasion SA was isolated from a milk sample from one animal primed by the i.n. route. It was just before the second immunisation.

Immunological analyses included measuring of the antibody responses in ELISA (see above). The results are shown in details in FIGS. 4:1 to 4:4.

Phagocytosis

Isolation and purification of leucocytes from bovine blood was carried out by the Ficoll centrifugation method as described by Guidry et al 1993 J Dairy Sci 76:1285-1289 and Lee et al 2005 Can J Vet Res 69:11-18. The cells were resuspended in Hanks basic solution (HBSS), checked for viability and the concentration was adjusted to $10 \times 10^6$ cells/ml. The selected strain of $S. aureus$ was first cultured on agar plates and subsequently in grown trypticase-soy-broth (TSB) (min 100 ml) in 37 C for 18 hrs. The bacteria were killed by incubation for 30 min. at 60 C in water bath. After 3 washes saline the bacterial suspension was adjusted in 1:10 dilution at an optical density of 2.0 at 540 nm.

FITC labelling of bacteria was carried out as described by Lee et al 2005 Can J Vet Res 69:11-18. The FITC-labelled bacteria were washed 3 times in Veronal-buffered saline with 0.15 mM calcium, 1 mM magnesium and 0.1% gelatine (GVBS) the concentration was determined at a dilution 1:10 to be OD 1.350 at 540 nm and finally kept in GVBS in aliquots of 1 ml at −80 C until use.

Phagocytosis; FITC labelled bacteria were thawed and sonicated for 30 sec. At 2.4 A and the concentration was adjusted to $1 \times 10^9$/ml. 50 µl of the test sera collected before and after two immunizations undiluted or diluted ¼ in HBSS were incubated the bacterial suspension and the cells as described by Lee et al 2005 Can J Vet Res 69:11-18. Controls included bacterial suspension incubated in HBSS, and bacterial suspension incubated with the cell suspension without serum. The incubation was done for 30 min at 37 C under careful shaking. Phagocytosis was stopped by adding ice-cold saline with 0.02% EDTA. Before reading in microscope the cells were treated 1% methylene blue to quenching of extra cellular fluorescence. The reading in fluorescence microscope was carried out on a minimum of 200 cells and the proportion of cells with bacteria was determined.

Results

Animals primed by the i.vag. route (FIG. 4:1) showed a low or no serum antibody response. In milk whey antibodies to FnBp were recorded after the first immunisation dominated by the IgG2 and IgA subclasses. No milk samples were collected before boost, since there is no milk production before calving. After the s.c. boost the antibody responses to FnBp in serum and milk were of short duration and dominated by IgG2 and IgA.

No or virtually no responses were detected in blood serum from animals primed by the i.n. route (FIG. 4:2). Antibodies against FnBp in milk whey were mainly recorded in the IgG2 and IgA subclasses. All animals given the primary immunisation by the i.n mode responded. After the s.c. boost the animals responded with clear-cut antibody rises in serum and in whey. The highest responses were in the IgG2 and IgA classes. The antibody levels declined towards the end of the experimental period.

The animals primed and boosted by the s.c. mode of administration obtained IgG1 and even higher levels of IgG2 and also high IgA in serum and milk whey (FIG. 4:3). After boost high levels of IgG1 and even higher levels of IgG2 and also high IgA in serum and milk whey indicating quality for protective immunity locally in the udder and circulating in the blood. Importantly, the serum antibodies lasted during the whole experimental period i.e. 7 to 10 months. Also the levels of milk whey antibodies lasted the experimental period i.e. up 8 months indicating that the experimental vaccination will cover the whole lactation period important for a prospective mastitis vaccine.

Phagocytosis was measured on serum from a cow in the group immunized twice by the s.c. route. 30% of PMN cells showed phagocytosis after incubation for 30 min. with bacteria and serum collected before the first immunization. An increase to 51% of PMN cells incubated for 30 min. with bacteria and serum collected after the second immunization showed phagocytosis. 4% PMN cells incubated with bacteria and no serum showed phagocytosis. 2% of PMN cells with no incubation time with bacteria and serum collected after the second immunization showed phagocytosis.

Discussion

The distribution of antibody responses in class and subclasses are of great importance to obtain optimal immune protective effect. Generally the IgG2 antibodies are considered of greatest importance to combat SA infection since this subclass promotes phagocytosis of the bacteria. All modes of immunisation promoted IgG2 and IgA FnBp specific antibodies both in milk whey and in blood serum. The antibody responses were considerably lower in serum and milk whey from animals that were primed i. vag and i.n. Unexpectedly high antibody levels were induced by two s.c. immunizations both in serum and mammary gland secretion with FnBp adjuvanted with iscom matrix including IgG1, IgG2 and the IgA subclasses. Immune responses of these magnitudes and quality have not been shown before in the bovine mammary gland with SA vaccines or any other vaccine. Also in blood serum these Ig subclasses were recorded. The s.c. mode of administration induced a long-lasting and superior immune response than the previously tested experimental vaccine (FIG. 4D), which was of short duration (Nelson et al. 1991). Of particular interest and value is the potent immune response in the mammary gland, which is not described with previous tested vaccine candidates against SA. The result from the functional phagocytosis test underlines that the important immune protective properties are evoked. The potent immuno enhancing effect of iscom matrix was not expected and facilitates an efficient vaccine production by avoiding the step of conjugation the FnBp polypeptides to iscom matrix.

There are two fibronectin binding protein FnBpA and FnBpB that are similarly organized. The construct used by Nelson et al consisted of a 60-65 kD protein conjugated with two IgG binding domains from the Staphylpcoccal protein A to form the fusion protein zzFnBpA to another part containing the presumptive T-cell epitopes to form zz-FnBpA-T and a zz-FnBpB, which contains a presumptive T-cell epitope. These polypeptides were conjugated to iscoms (Lövgren, K., Lindmark, J., Pipkorn, R. and Morein, B (1987) J. Immunol. Methods 98. We have used these polypeptides and found that they fragmented. One reason for the limitation of the Nelson construct we considered to be caused by the tendency to this fragmentation. The present fragment of FnBp of 16 kD is more stable and contains the repeats of the important DD region that facilitates the binding to fibronectin.

Conclusion

A truncated FnBp construct supplemented with an iscom matrix formulation induces after two s.c. immunizations high levels of high quality immune responses in the mammary gland and serum. There are strong immunological criteria that the prospective vaccine shall induce immune protection against SA infection in the bovine mammary gland. The technology enables an efficient production system that is of importance for a prospective vaccine.

Example 6

The Effect on the Whole SA-Cell and the α and β Haemolysins on the Immune Responses to FnBp and the Toxins SA causes chronic and persistent infections, which is facilitated by intrinsic properties of the pathogen based on ability to "hide" essential components for infection and survival for the immune system of the host. Moreover, pathogens causing persistent and chronic infections have capacity to guide the immune reactions of the host to allow its persistence. SA harbour a number of different components of immune regulatory properties and a wrong composition may cause low immune responses to one or all antigens included in the vaccine composition. As described above there are many components that are candidates for a SA vaccine. The first strategy is to use components that are isolated form the pathogen or produced as isolates vaccine antigens expressed by a cell in this case E. coli. The second approach is to use a powerful adjuvant in this case the iscom matrix. One prospective class of vaccine components are toxins. The fact that both α and β haemolysins (for the β haemolysin in 100% of the cases) of SA very frequently are identified in SA isolates from mastitis cases makes them strong vaccine candidates. Both toxins are excreted products and can be collected from the culture fluid where SA is growing. In this experiment the SA cells and culture fluid containing the α and β haemolysins were mixed with FnBp in a vaccine composition as laid out in Materials and Methods to explore the immunogenicity of FnBp and the toxins in this composition.

Materials and Methods

Experimental lay out. Twenty-five calves stationed at Öveds Kloster in the south of Sweden in the age of 4 to 7 months were immunized three times with 4 weeks intervals according to the immunization schedule below.

The SA bacteria and the culture fluid containing the α and β haemolysins were produced and kindly supplied by Karolinska Institutet MTC section of bacteriology headed by Professor Roland Möllby.

The immunizations were carried out s.c. prescapular at the side of the neck with 200 µg of FnBp or the mixture of FnBp and 10 exp 8/dose of Staphylococcus aureus cells and 50 µg each of the α and β haemolysins as described in the text table below. All vaccine formulations were adjuvanted with 1 mg iscom matrix per dose. The dose volume was 2 ml.

| | IMMUNIZATION SCHEME | | | | Test against animal groups |
|---|---|---|---|---|---|
| A/ | FnBp | FnBp | FnBp | 5 | FnBp & toxins |
| B/ | SA | FnBp | FnBp | 5 | FnBp & toxins |
| C/ | SA | SA | SA | 5 | FnBp & toxins |

-continued

|  | IMMUNIZATION SCHEME | | | | Test against animal groups |
|---|---|---|---|---|---|
| D/ | SA + Fn | SA + Fn | SA + Fn | 5 | FnBp & toxins |
| E/ | PBS | PBS | PBS | 5 | FnBp & toxins |

Fn: FnBp,
SA: *Staphylococcus aureus* cells and the α and β haemolysins,
PBS: Phosphate buffered solution The third immunizations are done for additional information about reaching the ceiling of the immune response, and information about possible suppression after repeated immunizations.

The evaluation of antibody responses to FnBp was carried out on serum by ELISA as described above. We need to know if SA as whole cell+toxins have a dominating effect on FnBp i.e. inhibit the immune response against FnBp.

Neutralization tests against the α and β haemolysins were carried out at the Karolinska Institutet MTC section of bacteriology headed by Professor Roland Möllby.

Results

The calves in this example are under one year of age and they did not respond or responded with very low antibody titres to FnBp supplemented with SA cells and the α and β haemolysins.

The immune response to FnBp measured by ELISA of group 1 is presented in FIG. 5:1. After the first immunization only animals in group 1 immunized with FnBp only and adjuvanted with iscom matrix responded both with IgM and IgG antibodies.

After the first boost clear-cut increases of the IgM, IgG1 and IgG2 responses were recorded in the animals vaccinated with FnBp alone. No animals primed with a composition containing FnBp and the *Staphylococcus aureus* cells and the α and β haemolysins showed immune response to FnBp (not shown).

After the third immunization tests to be done.

The immune response to α and β haemolysins were measured in a functional i.e. toxin neutralisation tests. The results are shown in FIG. 5:2. After the first immunization a low IgG response was recorded in animals in groups vaccines containing SA cells and toxins i.e. B, C and D. The antibody levers declined at the time for the second immunization. After the second immunization animals that have received two doses of toxins responded with high neutralization titres i.e. animals in groups C and D.

Discussion

This experiment shows that a mixture of *Staphylococcus aureus* cells and the α and β haemolysins suppresses the immune response to FnBp. In contrast all animals responded with high neutralizing antibodies against the α and β haemolysins. It is not clear, whether the toxins or other products in culture fluid or the whole cells or the combination of both cause the down regulation. The animals in this experiment were under one year of age. In a later experiment the animals were over one year up to two years old and these animals, which received FnBp supplemented either with SA cells or the α and β haemolysins, responded with high antibodies to FnBp (see example 7).

The suppression noticed in this experiment seems to be based on an active immune response i.e. with memory, since the animals in group B did not respond to the second dose.

In contrast the α and β haemolysins induced strong immune responses in all vaccine antigen combinations tested, which suggests that the combination of toxins and FnBp is a compatible and feasible vaccine composition. The possible use of whole SA cells in a vaccine composition needs further investigation. The results from example 7 indicates that older calves or cows might not react with a suppression to a vaccine antigen when SA cells or the α and β haemolysins are included in the vaccine formulation.

Conclusion

Previous experiments have shown that FnBp adjuvanted with iscom matrix is highly immunogenic in the bovine species, which is confirmed in this example. In the present example the immune response to FnBp is down regulated when FnBp is supplemented both with SA cells and the α and β haemolysins. It can be concluded from example 7 that a vaccine composition combining FnBp and the α and β haemolysins is highly immunogenic and so is a vaccine combination FnBp SA cells, when the antibody response is measured against FnBp. It is conceivable that, cattle over the age of one year, do not react with the suppression noted in younger animals immunized with FnBp supplemented SA cells in combination with the α and β haemolysins.

Example 7

In example 6 we have seen that a mixture of α and β haemolysins and whole SA cells in an experimental vaccine down-regulated the immune response to the third component i.e. FnBp. Since both α and β haemolysins and whole SA cells were included it was not clear whether one or the other or the combination of both toxins and cells were responsible for the suppressive effect. In this example the suppressive respectively the compatible or enhancing effects are further investigated by combining FnBp with either the toxins or the whole SA cells. For that purpose an experiment was set up as described in materials and methods. All experimental vaccines were adjuvanted with iscom matrix.

Materials and Methods

Experimental lay out. 15 calves, stationed at the Mosta Farm east of Uppsala in Sweden, in the age of 1 to 2 years were immunized two times with 6 weeks intervals according to the immunization schedule below.

The SA bacteria and the culture fluid containing the α and β haemolysins were produced and kindly supplied by Karolinska Institutet MTC section of bacteriology headed by Professor Roland Möllby.

The immunizations were carried out s.c. prescapular at the side of the neck with 200 μg of FnBp or the mixture of FnBp and 10 exp 8/dose of *Staphylococcus aureus* cells or the mixture of FnBp with 50 μg each of the α and β haemolysins as described in the text table below. All vaccine formulations were adjuvanted with 1 mg iscom matrix per dose. The dose volume was 2 ml.

|  | IMMUNIZATION SCHEME | | | Test against animal groups |
|---|---|---|---|---|
| A/ | FnBp | FnBp | 5 | FnBp & toxins |
| B/ | SA + Fn | SA + Fn | 5 | FnBp & toxins |
| C/ | Tox + Fn | Tox + Fn | 5 | FnBp & toxins |
| D/ | PBS | PBS | 5 | FnBp & toxins |

Fn: FnBp,
SA: *Staphylococcus aureus*,
Tox: the α and β haemolysins
PBS: Phosphate buffered solution Results The immune response to FnBp measured by ELISA is presented in FIG. 6:1. Three weeks after the first immunization all animals responded with comparatively high antibody titres against FnBp including all immunoglobulin classes tested i.e. IgM, IgG1 and IgG2.

With such a primary immune response all accumulated experience tell us that after the second immunisation a substantial increase of the IgG subclass response will occur. The data from the second immunization are pending.

Discussion

This experiment shows that a mixture of *Staphylococcus aureus* cells and the α and β haemolysins separately do not suppress the immune response to FnBp. In example 6 it was clearly shown that the toxin component or other products in culture fluid and the whole cells in combination down regulated the immune response in all immunoglobulin classes tested. The suppression demonstrated in example 6 seems to be based on an active immune response including immune memory cells.

In example 6 it was also shown that the α and β haemolysins induced strong immune responses in all vaccine antigen combinations, which suggests that the combination of toxins and FnBp is a compatible and feasible vaccine composition. The results from this example shows that the use of whole SA cells in a vaccine composition is possible provided the factor(s) causing suppression in the vaccine antigen composition tested in some groups in example 6 are identified and excluded from the prospective vaccine containing whole cells. It should be noted that the antibody response to FnBp supplemented with both SA cells and the α and β haemolysins is low indicating a suppression of immune response to FnBp. It should be noted that the calves in example 6 were under one year of age, while the animals in this example 7 were older i.e. 1 to 2 years. The younger animals might still have a not fully developed immune system or maternal antibodies not reflected by FnBp antibodies.

In a number of formulations the iscom matrix adjuvanted experimental vaccines have included FnBp and toxins (see examples 3 and 4). In mouse models very potent immune responses were evoked both to FnBp and the included toxins. Thus, the accumulated results strongly show that strong immune responses are induced by prospective vaccine formulations including an adhesion factor and other components adjuvanted with iscom formulations.

Conclusion

High antibody levels were induced in animals in the age to go into lactation against FnBp when mixed either with toxins or with whole SA bacterial cells. Thus, a SA vaccine based on several antigen components is feasible.

TABLE 1:1

Lay out of the immunization of Balb/C mice with fibronectin binding protein (FnBp). The mice were immunized twice s.c. four weeks apart with the respective vaccine candidates

| Group | Antigen | Adjuvant | No of animals |
|---|---|---|---|
| 1 | FnBp (2 ug/dose) | no adjuvant | 8 |
| 2 | | 1% Al(OH)$_3$ | 8 |
| 3 | | 6 ug Matrix-Q | 8 |
| 4 | | 6 ug Matrix-C | 8 |
| 5 | | 4 ug Matrix-LowTox* | 8 |

LowTox formulation consists of a mixture of 0.6 ug Matrix-C + 3.4 ug Matrix-A in separate particles.

TABLE 2:1

Lay out of the immunization of Balb/C mice tetanus toxoid (TT). The mice were immunized twice s.c four weeks apart with the respective vaccine candidates

| Group | Antigen | Adjuvant | No of animals |
|---|---|---|---|
| 1 | TT (0.5 Lf/dose) | No adjuvant | 8 |
| 2 | | 1% Al(OH)$_3$ | 8 |
| 3 | | 6 ug Matrix -Q | 8 |
| 4 | | 6 ug Matrix -C | 8 |
| 5 | | 4 ug Matrix-LowTox* | 8 |

LowTox formulation consists of a mixture of 0.6 ug Matrix-C + 3.4 ug Matrix-A in separate particles.

TABLE 3:1

Lay out of the immunization of Balb/C mice with difteri toxiod-(DT). The mice were immunized twice s.c. four weeks apart with the respective vaccine candidates

| Group | Antigen | Adjuvant | No of animals |
|---|---|---|---|
| 1 | DT (1 ug/dose) | No adjuvant | 8 |
| 2 | | 1% Al(OH)$_3$ | 8 |
| 3 | | 6 ug Matrix -Q | 8 |
| 4 | | 6 ug Matrix X-C | 8 |
| 5 | | 4 ug Matrix-LowTox* | 8 |

LowTox formulation consists of a mixture of 0.6 ug Matrix-C + 3.4 ug Matrix-A in separate particles.

The invention claimed is:

1. A method for vaccination of an individual, comprising administering to the individual a composition comprising: (i) at least one fibronectin binding protein, and/or at least one truncated fibronectin binding protein, and/or at least one fibronectin binding peptide, that comprise at least one fibronectin binding domain, and (ii) at least one iscom matrix complex, wherein the at least one iscom matrix complex does not comprise fibronectin binding protein, truncated fibronectin binding protein, or fibronectin binding peptide, and wherein the individual is a mammal selected from the group consisting of human, cattle, sheep, and goat.

2. The method of claim 1 wherein the composition further comprises at least one lipid and at least one saponin, whereby the at least one lipid and the at least one saponin may be in complex, solution or suspension.

3. The method according to claim 1, wherein the fibronectin binding protein, the truncated fibronectin binding protein, and/or the fibronectin binding peptide comprises one or more fibronectin binding domains from *Staphylococcus aureus, Streptococcus pyogenes, Streptococcus dysgalactiae, Streptococcus agalactiae, Streptococcus uberis* or coagulase negative *Staphylococcus*.

4. The method according to claim 1, wherein the fibronectin binding domain is selected from the D domains from fibronectin binding protein A or B from *Staphylococcus aureus*, the A domains from fibronectin binding protein A from *Streptococcus dysgalactiae*, the B domains from fibronectin binding protein B *Streptococcus dysgalactiae*, or the P domains from fibronectin binding protein *Streptococcus pyogenes*.

5. The method according to claim 1, wherein the composition further comprises at least one other antigen.

6. The method according to claim 5, wherein the antigens are in the form of whole cells of and/or antigenic components from microorganisms.

7. The method according to claim 5, wherein the antigens are in the form of antigenic components that do not down regulate the immune system or antigenic components that down regulate the immune system.

8. The method according to claim 6, wherein the whole cells are from *Staphylococcus aureus, Streptococcus pyogenes, Streptococcus dysgalactiae, Streptococcus agalactiae, Streptococcus uberis* or coagulase negative *Staphylococcus*.

9. The method according to claim 7, wherein the components that do not down regulate the immune system are selected from adhesins or pore forming factors, or the components that down regulate the immune system are selected from superantigens, capsular antigens, endotoxins, exotoxins or extra cellular enzymes.

10. The method according to claim 9, wherein the adhesins are chosen from clumping factor, external fibrin binding protein, A and B Adhesins to fibrinogen, Coagulase, fibrogen binding protein, Fibronectin binding protein A and B, collagen binding protein; Elastin binding protein, MHC analogous protein, Polysaccharide intracellular adhesin, intracellular adhesion factor for biofilm formation, Protein A Capsular polysaccharides or Techoic acid.

11. The method according to claim 9, wherein the pore forming factors are chosen from alpha-haemolysin, beta-haemolysin, gamma-haemolysin, delta-haemolysin, Phospholipase C (plc; lysis of host cell), Elastase (sepA) tissue invasion, or Hyaluronidase (hysA) tissue invasion.

12. The method according to claim 9, wherein the exotoxins and extracellular enzymes are chosen from enterotoxins A to E, H, Toxin shock syndrome toxin-1, Lipase, Panton-Vallentine leukociddin, Staphylokinase, *Staphylococcus aureus*, and α-och β-toxins.

13. The method according to claim 1, wherein the iscom matrix complex comprises one or more glycoside fragments from Quil A.

14. The method according to claim 13, wherein at least two glycoside fragments from Quil A are complex bound in different iscom matrix particles.

15. The method according to claim 13, wherein the iscom matrix complex comprises subfragment A and/or subfragment C of Quil A.

16. The method according to claim 1, wherein the iscom matrix complex comprises crude Quil A.

17. The method according to claim 1, wherein the composition further comprises at least one antigen affecting the udder.

18. The method according to claim 1, wherein the composition further comprises a pharmaceutically acceptable carrier, diluents, excipient or additive.

19. The method of claim 1, wherein antibodies are established in serum and/or udder and/or milk.

20. The method of claim 1, wherein the at least one fibronectin binding protein is presented in the form of whole cells.

21. The method according to claim 17, wherein the antigen affecting the udder is selected from *Streptococcus uberis, Streptococcus dysgalacti, Streptococcus agalacti, Klebsiella* sp.p, or *E. coli*.

22. The method according to claim 1, wherein the vaccine is against *Staphylococcus aureus*.

* * * * *

UNITED STATES PATENT AND TRADEMARK OFFICE
CERTIFICATE OF CORRECTION

PATENT NO. : 8,007,806 B2  
APPLICATION NO. : 11/795662  
DATED : August 30, 2011  
INVENTOR(S) : Bror Morein et al.

Page 1 of 1

It is certified that error appears in the above-identified patent and that said Letters Patent is hereby corrected as shown below:

Column 16, line 48, at the end of line 48, after the sequence listing, please insert --(SEQ ID NO:5)--;

Column 16, line 53, at the end of line 53, after the sequence listing, please insert --(SEQ ID NO:6)--.

Signed and Sealed this  
Fifteenth Day of May, 2012

David J. Kappos  
*Director of the United States Patent and Trademark Office*

UNITED STATES PATENT AND TRADEMARK OFFICE
CERTIFICATE OF CORRECTION

PATENT NO. : 8,007,806 B2
APPLICATION NO. : 11/795662
DATED : August 30, 2011
INVENTOR(S) : Bror Morein et al.

It is certified that error appears in the above-identified patent and that said Letters Patent is hereby corrected as shown below:

On the Title Page

Item (75) Inventors: The sixth inventor:
"Carlos Concha Baschunan, Santiago (CL)"
Should read:
-- Carlos Concha Bascunan, Santiago (CL) --

Signed and Sealed this
Twenty-eighth Day of February, 2023

Katherine Kelly Vidal
*Director of the United States Patent and Trademark Office*

SEQUENCE LISTING

```
<160> NUMBER OF SEQ ID NOS: 10

<210> SEQ ID NO 1
<211> LENGTH: 38
<212> TYPE: DNA
<213> ORGANISM: Artificial
<220> FEATURE:
<223> OTHER INFORMATION: Synthetic Primer Forward

<400> SEQUENCE: 1
cgggatcctg cagcatcaga acaaaagaca actacagt                           38

<210> SEQ ID NO 2
<211> LENGTH: 39
<212> TYPE: DNA
<213> ORGANISM: Artificial
<220> FEATURE:
<223> OTHER INFORMATION: Synthetic Primer Reverse
```

-continued

<400> SEQUENCE: 2
gtaagcttat gctttgtgat tcttttatt tctgcgtaa    39

<210> SEQ ID NO 3
<211> LENGTH: 37
<212> TYPE: DNA
<213> ORGANISM: Artificial
<220> FEATURE:
<223> OTHER INFORMATION: Synthetic Primer Forward

<400> SEQUENCE: 3
cgggatccat ggcatcagaa caaaagacaa ctacagt    37

<210> SEQ ID NO 4
<211> LENGTH: 37
<212> TYPE: DNA
<213> ORGANISM: Artificial
<220> FEATURE:
<223> OTHER INFORMATION: Synthetic Primer Reverse

<400> SEQUENCE: 4
gagctcgagt ggcacgattg gaggtgttgt atcttct    37

<210> SEQ ID NO 5
<211> LENGTH: 39
<212> TYPE: DNA
<213> ORGANISM: Artificial
<220> FEATURE:
<223> OTHER INFORMATION: Synthetic Primer Forward

<400> SEQUENCE: 5
cgggatccat ggaaggtggc caaaatagcg gtaaccagt    39

<210> SEQ ID NO 6
<211> LENGTH: 39
<212> TYPE: DNA
<213> ORGANISM: Artificial
<220> FEATURE:
<223> OTHER INFORMATION: Synthetic Primer Reverse

<400> SEQUENCE: 6
gagctcgaga ggtgttgtat cttcttcaat cgtttgttg    39

<210> SEQ ID NO 7
<211> LENGTH: 141
<212> TYPE: PRT
<213> ORGANISM: Staphylococcus aureus
<220> FEATURE:
<221> NAME/KEY: misc_feature
<223> OTHER INFORMATION: FnBpA

<400> SEQUENCE: 7

Met Glu Gly Gly Gln Asn Ser Gly Asn Gln Ser Phe Glu Glu Asp Thr
1               5                   10                  15

Glu Glu Asp Lys Pro Lys Tyr Glu Gln Gly Gly Asn Ile Val Asp Ile
                20                  25                  30

Asp Phe Asp Ser Val Pro Gln Ile His Gly Gln Asn Lys Gly Asn Gln
            35                  40                  45

Ser Phe Glu Glu Asp Thr Glu Lys Asp Lys Pro Lys Tyr Glu His Gly
        50                  55                  60

Gly Asn Ile Ile Asp Ile Asp Phe Asp Ser Val Pro His Ile His Gly
65                  70                  75                  80

Phe Asn Lys His Thr Glu Ile Ile Glu Glu Asp Thr Asn Lys Asp Lys
                85                  90                  95

```
Pro Ser Tyr Gln Phe Gly Gly His Asn Ser Val Asp Phe Glu Glu Asp
            100                 105                 110

Thr Leu Pro Lys Val Ser Gly Gln Asn Glu Gly Gln Gln Thr Ile Glu
        115                 120                 125

Glu Asp Thr Thr Pro Leu Glu His His His His His His
    130                 135                 140

<210> SEQ ID NO 8
<211> LENGTH: 141
<212> TYPE: PRT
<213> ORGANISM: Staphylococcus aureus
<220> FEATURE:
<221> NAME/KEY: misc_feature
<223> OTHER INFORMATION: FnBpB

<400> SEQUENCE: 8

Met Glu Gly Gly Gln Asn Ser Gly Asn Gln Ser Phe Glu Glu Asp Thr
1               5                   10                  15

Glu Glu Asp Lys Pro Lys Tyr Glu Gln Gly Gly Asn Ile Val Asp Ile
            20                  25                  30

Asp Phe Asp Ser Val Pro Gln Ile His Gly Gln Asn Asn Gly Asn Gln
        35                  40                  45

Ser Phe Glu Glu Asp Thr Glu Lys Asp Lys Pro Lys Tyr Glu Gln Gly
    50                  55                  60

Gly Asn Ile Ile Asp Ile Asp Phe Asp Ser Val Pro His Ile His Gly
65                  70                  75                  80

Phe Asn Lys His Thr Glu Ile Ile Glu Glu Asp Thr Asn Lys Asp Lys
                85                  90                  95

Pro Asn Tyr Gln Phe Gly Gly His Asn Ser Val Asp Phe Glu Glu Asp
            100                 105                 110

Thr Leu Pro Gln Val Ser Gly His Asn Glu Gly Gln Gln Thr Ile Glu
        115                 120                 125

Glu Asp Thr Thr Pro Leu Glu His His His His His His
    130                 135                 140

<210> SEQ ID NO 9
<211> LENGTH: 136
<212> TYPE: PRT
<213> ORGANISM: Staphylococcus aureus
<220> FEATURE:
<221> NAME/KEY: misc_feature
<223> OTHER INFORMATION: FnBpA Cys-N

<400> SEQUENCE: 9

Met Ala Cys Glu Gly Gly Gln Asn Ser Gly Asn Gln Ser Phe Glu Glu
1               5                   10                  15

Asp Thr Glu Glu Asp Lys Pro Lys Tyr Glu Gln Gly Gly Asn Ile Val
            20                  25                  30

Asp Ile Asp Phe Asp Ser Val Pro Gln Ile His Gly Gln Asn Lys Gly
        35                  40                  45

Asn Gln Ser Phe Glu Glu Asp Thr Glu Lys Asp Lys Pro Lys Tyr Glu
    50                  55                  60

His Gly Gly Asn Ile Ile Asp Ile Asp Phe Asp Ser Val Pro His Ile
65                  70                  75                  80

His Gly Phe Asn Lys His Thr Glu Ile Ile Glu Glu Asp Thr Asn Lys
                85                  90                  95

Asp Lys Pro Ser Tyr Gln Phe Gly Gly His Asn Ser Val Asp Phe Glu
            100                 105                 110
```

```
Glu Asp Thr Leu Pro Lys Val Ser Gly Gln Asn Glu Gly Gln Gln Thr
        115                 120                 125

Ile Glu Glu Asp Thr Thr Pro Gly
    130                 135

<210> SEQ ID NO 10
<211> LENGTH: 135
<212> TYPE: PRT
<213> ORGANISM: Staphylococcus aureus
<220> FEATURE:
<221> NAME/KEY: misc_feature
<223> OTHER INFORMATION: FnBpA Cys-C

<400> SEQUENCE: 10

Met Glu Gly Gly Gln Asn Ser Gly Asn Gln Ser Phe Glu Glu Asp Thr
1               5                   10                  15

Glu Glu Asp Lys Pro Lys Tyr Glu Gln Gly Gly Asn Ile Val Asp Ile
            20                  25                  30

Asp Phe Asp Ser Val Pro Gln Ile His Gly Gln Asn Lys Gly Asn Gln
        35                  40                  45

Ser Phe Glu Glu Asp Thr Glu Lys Asp Lys Pro Lys Tyr Glu His Gly
    50                  55                  60

Gly Asn Ile Ile Asp Ile Asp Phe Asp Ser Val Pro His Ile His Gly
65                  70                  75                  80

Phe Asn Lys His Thr Glu Ile Ile Glu Glu Asp Thr Asn Lys Asp Lys
                85                  90                  95

Pro Ser Tyr Gln Phe Gly Gly His Asn Ser Val Asp Phe Glu Glu Asp
            100                 105                 110

Thr Leu Pro Lys Val Ser Gly Gln Asn Glu Gly Gln Gln Thr Ile Glu
        115                 120                 125

Glu Asp Thr Thr Pro Cys Gly
    130                 135
```